US007951560B2

(12) United States Patent
Myette et al.

(10) Patent No.: US 7,951,560 B2
(45) Date of Patent: *May 31, 2011

(54) DELTA 4,5 GLYCURONIDASE COMPOSITIONS AND METHODS RELATED THERETO

(75) Inventors: James R. Myette, Belmont, MA (US); Zachary Shriver, Cambridge, MA (US); Ganesh Venkataraman, Bedford, MA (US); Ram Sasisekharan, Cambridge, MA (US); Maitland W. McLean, Orkney (GB)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/616,764

(22) Filed: Nov. 11, 2009

(65) Prior Publication Data

US 2010/0129868 A1 May 27, 2010

Related U.S. Application Data

(60) Continuation of application No. 11/402,491, filed on Apr. 11, 2006, now Pat. No. 7,695,711, which is a division of application No. 10/429,921, filed on May 5, 2003, now abandoned.

(60) Provisional application No. 60/377,488, filed on May 3, 2002.

(51) Int. Cl.
*A01N 63/00* (2006.01)
*C12P 21/06* (2006.01)
*C12N 9/00* (2006.01)
*C12N 9/26* (2006.01)
*C12N 1/20* (2006.01)
*C12N 15/00* (2006.01)
*C07H 21/02* (2006.01)

(52) U.S. Cl. ...... 435/69.1; 424/93.1; 435/183; 435/201; 435/252.3; 435/320.1; 536/23.1

(58) Field of Classification Search .................. None
See application file for complete search history.

(56) References Cited

U.S. PATENT DOCUMENTS

| 6,217,863 | B1 | 4/2001 | Godavarti et al. |
| 6,597,996 | B1 | 7/2003 | Venkataraman et al. |
| 6,869,789 | B2 | 3/2005 | Liu et al. |
| 6,962,699 | B2 | 11/2005 | Pojasek et al. |
| 7,056,504 | B1 | 6/2006 | Sasisekharan et al. |
| 7,083,937 | B2 | 8/2006 | Sasisekharan et al. |
| 7,105,334 | B2 | 9/2006 | Pojasek et al. |
| 7,110,889 | B2 | 9/2006 | Venkataraman et al. |
| 7,117,100 | B2 | 10/2006 | Venkataraman et al. |
| 7,129,335 | B2 | 10/2006 | Pojasek et al. |
| 7,139,666 | B2 | 11/2006 | Venkataraman |
| 7,247,445 | B2 | 7/2007 | Sasisekharan et al. |
| 7,270,815 | B2 | 9/2007 | Sasisekharan et al. |
| 7,390,633 | B2 | 6/2008 | Liu et al. |
| 7,396,824 | B2 | 7/2008 | Sasisekharan et al. |
| 7,399,604 | B2 | 7/2008 | Sasisekharan et al. |
| 7,412,332 | B1 | 8/2008 | Venkataraman et al. |
| 7,429,474 | B2 | 9/2008 | Sasisekharan et al. |
| 7,455,986 | B2 | 11/2008 | Liu et al. |
| 7,504,247 | B2 | 3/2009 | Sasisekharan et al. |
| 7,507,570 | B2 | 3/2009 | Prabhakar et al. |
| 7,508,206 | B2 | 3/2009 | Sasisekharan et al. |
| 7,553,950 | B2 | 6/2009 | Prabhakar et al. |
| 7,560,106 | B2 | 7/2009 | Sasisekharan et al. |
| 7,585,642 | B2 | 9/2009 | Sasisekharan et al. |
| 7,592,152 | B2 | 9/2009 | Prabhakar et al. |
| 2002/0122793 | A1 | 9/2002 | Liu et al. |
| 2002/0128225 | A1 | 9/2002 | Liu et al. |
| 2002/0169143 | A1 | 11/2002 | Sasisekharan et al. |
| 2003/0008820 | A1 | 1/2003 | Kwan et al. |
| 2003/0099628 | A1 | 5/2003 | Liu et al. |
| 2003/0161884 | A1 | 8/2003 | Rosenberg et al. |
| 2003/0191587 | A1 | 10/2003 | Venkataraman et al. |
| 2004/0091471 | A1 | 5/2004 | Myette et al. |
| 2004/0091472 | A1 | 5/2004 | Pojasek et al. |
| 2004/0092037 | A1 | 5/2004 | Sasisekharan et al. |
| 2004/0197933 | A1 | 10/2004 | Venkataraman et al. |
| 2004/0204869 | A1 | 10/2004 | Venkataraman et al. |
| 2005/0037376 | A1 | 2/2005 | Sasisekharan et al. |
| 2005/0214276 | A9 | 9/2005 | Myette et al. |
| 2005/0227320 | A1 | 10/2005 | Pojasek et al. |
| 2005/0233402 | A1 | 10/2005 | Liu et al. |
| 2005/0233419 | A1 | 10/2005 | Pojasek et al. |
| 2006/0024664 | A1 | 2/2006 | Sasisekharan et al. |
| 2006/0057638 | A1 | 3/2006 | Bosques et al. |
| 2006/0067927 | A1 | 3/2006 | Chandrasekaran et al. |
| 2006/0067928 | A1 | 3/2006 | Liu et al. |
| 2006/0078959 | A1 | 4/2006 | Prabhakar et al. |
| 2006/0083711 | A1 | 4/2006 | Berry et al. |
| 2006/0105430 | A1 | 5/2006 | Sasisekharan et al. |

(Continued)

FOREIGN PATENT DOCUMENTS

WO WO 97/16556 A1 5/1997

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
[No Author Listed] "Heparan sulfate." http://en.wikipedia.org/wiki/Heparan. Accessed May 22, 2008. 5 pages.
[No Author Listed] "Heparin." http://en.wikipedia.org/wiki/Heparin. Accessed May 26, 2008. 10 pages.
Binari et al., Genetic evidence that heparin-like glycosaminoglycans are involved in wingless signaling. Development. Jul. 1997;124(13):2623-32.
Branden et al., Introduction to protein structure. Garland Publishing Inc., New York, 1991, p. 247.
Brown, Hybridization analysis of DNA blots. Curr Prot Molec Biol. 1993:2.10.1-2.10.16.
Bruce et al., Flavobacterium heparinum 3-O-sulphatase for N-substituted glucosamine 3-O-sulphate. Eur J Biochem. Apr. 15, 1985;148(2):359-65.

(Continued)

Primary Examiner — Christian L Fronda
(74) Attorney, Agent, or Firm — Wolf, Greenfield & Sacks, P.C.

(57) ABSTRACT

The invention relates to Δ4,5 glycuronidase, related compositions, and methods of use thereof.

18 Claims, 10 Drawing Sheets

U.S. PATENT DOCUMENTS

| | | | |
|---|---|---|---|
| 2006/0127950 | A1 | 6/2006 | Bosques et al. |
| 2006/0154894 | A1 | 7/2006 | Berry et al. |
| 2006/0177885 | A1 | 8/2006 | Myette et al. |
| 2006/0177910 | A1 | 8/2006 | Myette et al. |
| 2006/0177911 | A1 | 8/2006 | Myette et al. |
| 2006/0182734 | A1 | 8/2006 | Liu et al. |
| 2006/0183713 | A1 | 8/2006 | Liu et al. |
| 2006/0183891 | A1 | 8/2006 | Myette et al. |
| 2006/0292130 | A1 | 12/2006 | Sasisekharan et al. |
| 2006/0292655 | A1 | 12/2006 | Sasisekharan et al. |
| 2006/0292673 | A1 | 12/2006 | Sasisekharan et al. |
| 2007/0004012 | A1 | 1/2007 | Sasisekharan et al. |
| 2007/0020243 | A1 | 1/2007 | Sengupta et al. |
| 2007/0065424 | A1 | 3/2007 | Pojasek et al. |
| 2007/0065921 | A1 | 3/2007 | Sasisekharan et al. |
| 2007/0066769 | A1 | 3/2007 | Venkataraman et al. |
| 2007/0148157 | A1 | 6/2007 | Prabhakar et al. |
| 2007/0148158 | A1 | 6/2007 | Sasisekharan et al. |
| 2007/0148740 | A1 | 6/2007 | Prabhakar et al. |
| 2007/0161073 | A1 | 7/2007 | Sasisekharan et al. |
| 2007/0202563 | A1 | 8/2007 | Prabhakar et al. |
| 2007/0224670 | A1 | 9/2007 | Prabhakar et al. |
| 2008/0071148 | A1 | 3/2008 | Bosques et al. |
| 2008/0278164 | A1 | 11/2008 | Sasisekharan et al. |
| 2008/0301178 | A1 | 12/2008 | Venkataraman et al. |
| 2009/0045811 | A1 | 2/2009 | Sasisekharan et al. |
| 2009/0081635 | A1 | 3/2009 | Liu et al. |
| 2009/0105463 | A1 | 4/2009 | Berry et al. |
| 2009/0119027 | A1 | 5/2009 | Venkataraman et al. |
| 2009/0156477 | A1 | 6/2009 | Berry et al. |
| 2009/0269326 | A1 | 10/2009 | Myette et al. |

FOREIGN PATENT DOCUMENTS

| | | |
|---|---|---|
| WO | WO 00/12726 A2 | 3/2000 |
| WO | WO 00/40225 A2 | 7/2000 |
| WO | WO 00/65521 A2 | 11/2000 |
| WO | WO 01/02443 A1 | 1/2001 |
| WO | WO 01/66772 A2 | 9/2001 |
| WO | WO 01/91729 A1 | 12/2001 |
| WO | WO 02/23190 A2 | 3/2002 |
| WO | WO 02/32406 A2 | 4/2002 |
| WO | WO 02/077199 A2 | 10/2002 |
| WO | WO 03/102160 A3 | 12/2003 |
| WO | WO 2004/055491 A2 | 7/2004 |
| WO | WO 2004/062592 A2 | 7/2004 |
| WO | WO 2004/069152 A2 | 8/2004 |
| WO | WO 2005/087920 A2 | 9/2005 |
| WO | WO 2005/110438 A2 | 11/2005 |
| WO | WO 2005/111627 A2 | 11/2005 |
| WO | WO 2006/076627 A2 | 7/2006 |
| WO | WO 2006/083328 A2 | 8/2006 |
| WO | WO 2006/088491 A2 | 8/2006 |
| WO | WO 2006/089206 A1 | 8/2006 |
| WO | WO 2006/105313 A2 | 10/2006 |
| WO | WO 2006/105315 A2 | 10/2006 |
| WO | WO 2007/044471 A2 | 4/2007 |
| WO | WO 2007/120478 A2 | 10/2007 |

OTHER PUBLICATIONS

Bruce et al., Flavobacterium heparinum 6-O-sulphatase for N-substituted glucosamine 6-O-sulphate. Eur J Biochem. Oct. 1, 1985;152(1):75-82.

Chica et al., Semi-rational approaches to engineering enzyme activity: combining the benefits of directed evolution and rational design. Curr Opin Biotechnol. Aug. 2005;16(4):378-84. Review.

Dietrich et al., Enzymic degradation of heparin. A glucosaminidase and a glycuronidase from Flavobacterium heparinum. Biochemistry. May 1969;8(5):2089-94.

Dietrich et al., Sequential degradation of heparin in Flavobacterium heparinum. Purification and properties of five enzymes involved in heparin degradation. J Biol Chem. Sep. 25, 1973;248(18):6408-15.

Ernst et al., Enzymatic degradation of glycosaminoglycans. Crit Rev Biochem Mol Biol. 1995;30(5):387-444.

Ernst et al., Expression in *Escherichia coli*, purification and characterization of heparinase I from Flavobacterium heparinum. Biochem J. Apr. 15, 1996;315 ( Pt 2):589-97.

Feingold et al., Conformational aspects of the reaction mechanisms of polysaccharide lyases and epimerases. FEBS Lett. Nov. 2, 1987;223(2):207-11. Review.

Gacesa, Alginate-modifying enzymes: a proposed unified mechanism of action for the lyases and epimerases. FEBS Letters. 1987;212(2):199-202.

Genbank Submission; NIH/NCBI, Accession No. AAO79763; Xu et al.; Feb. 9, 2006.

Genbank Submission; NIH/NCBI, Accession No. AB019619; Hashimoto et al.; Sep. 11, 1999.

Genbank Submission; NIH/NCBI, Accession No. AE006517; Ferretti et al.; Jun. 3, 2004.

Genbank Submission; NIH/NCBI, Accession No. AE008410; Hoskins et al.; Sep. 13, 2001.

Genbank Submission; NIH/NCBI, Accession No. AJ271692; Eastwood et al.; Jan. 2, 1002.

Genbank Submission; NIH/NCBI, Accession No. AP001514; Takami et al.; Jul. 14, 2004.

Genbank Submission; NIH/NCBI, Accession No. BH384072; Hong et al.; Dec. 10, 2001.

Genbank Submission; NIH/NCBI, Accession No. NP 242920; Takami et al.; Dec. 3, 2005.

Genbank Submission; NIH/NCBI, Accession No. NP 344858; Tettelin et al.; Nov. 22, 2006.

Gu et al., Purification, characterization and specificity of chondroitin lyases and glycuronidase from Flavobacterium heparinum. Biochem J. Dec. 1, 1995;312 ( Pt 2):569-77.

Habuchi et al., Diversity and functions of glycosaminoglycan sulfotransferases. Biochim Biophys Acta. Apr. 6, 2000;1474(2):115-27.

Hashimoto et al., Unsaturated glucuronyl hydrolase of *Bacillus* sp. GL1: novel enzyme prerequisite for metabolism of unsaturated oligosaccharides produced by polysaccharide lyases. Arch Biochem Biophys. Aug. 15, 1999;368(2):367-74.

Hovingh et al., Specificity of flavobacterial glycuronidases acting on disaccharides derived from glycosaminoglycans. Biochem J. Aug. 1, 1977;165(2):287-93.

Huang et al., Active site of chondroitin AC lyase revealed by the structure of enzyme-oligosaccharide complexes and mutagenesis. Biochemistry. Feb. 27, 2001;40(8):2359-72.

Koeller et al., Complex carbohydrate synthesis tools for glycobiologists: enzyme-based approach and programmable one-pot strategies. Glycobiology. Nov. 2000;10(11):1157-69. Review.

Lin et al., Heparan sulfate proteoglycans are essential for FGF receptor signaling during Drosophila embryonic development. Development. Sep. 1999;126(17):3715-23.

Lindahl et al., Common binding sites for beta-amyloid fibrils and fibroblast growth factor-2 in heparan sulfate from human cerebral cortex. J Biol Chem. Oct. 22, 1999;274(43):30631-5.

Linhardt et al., Polysaccharide lyases. Appl Biochem Biotechnol. Apr. 1986;12(2):135-76.

Linker et al., The enzymatic degradation of heparin and heparitin sulfate. I. The fractionation of a crude heparinase from flavobacteria. J Biol Chem. Oct. 1965;240(10):3724-8.

Lohse, et al., Purification and characterization of heparin lyases from Flavobacterium heparinum. J Biol Chem. Dec. 5, 1992;267(34):24347-55.

McLean et al., Action of heparinase II on pig mucosal heparin. Proc. Of the 8th International Symposium on Glycoconjugates. 1985. Abstract 73-74.

McLean et al., Enzymic removal of 2-O-sulphato-?4,5-glycuronic acid residues from heparin oligosaccharides. Proceedings of the 7th International Symposium of Glycoconjugates. Lund, Sweden. 1983;68-9.

McLean et al., Flavobacterium heparinum 2-O-sulphatase for 2-O-sulphato-delta 4,5-glycuronate-terminated oligosaccharides from heparin. Eur J Biochem. Dec. 17, 1984;145(3):607-15.

Myette et al., Molecular cloning of the heparin/heparan sulfate delta 4,5 unsaturated glycuronidase from Flavobacterium heparinum, its recombinant expression in *Escherichia coli*, and biochemical determination of its unique substrate specificity. Biochemistry. Jun. 11, 2002;41(23):7424-34.

Nielsen et al., Identification of prokaryotic and eukaryotic signal peptides and prediction of their cleavage sites. Protein Eng. Jan. 1997;10(1):1-6.

Petitou et al., Synthetic oligosaccharides having various functional domains: potent and potentially safe heparin mimetics. Bioorg Med Chem Lett. Apr. 19, 1999;9(8):1161-6.

Pojasek et al., Histidine 295 and histidine 510 are crucial for the enzymatic degradation of heparan sulfate by heparinase III. Biochemistry. Apr. 11, 2000;39(14):4012-9.

Rabenstein, Heparin and heparan sulfate: structure and function. Nat. Prod. Rep. Jan. 2002;19(3):312-31.

Razi et al., Structural and functional properties of heparin analogues obtained by chemical sulphation of *Escherichia coli* K5 capsular polysaccharide. Biochem J. Jul. 15, 1995;309 ( Pt 2):465-72.

Rhomberg et al., Mass spectrometric and capillary electrophoretic investigation of the enzymatic degradation of heparin-like glycosaminoglycans. Proc Natl Acad Sci U S A. Apr. 14, 1998;95(8):4176-81.

Sambrook et al., Molecular Cloning: A Laboratory Manual. 2nd Edition. 1989.

Sasisekharan et al., Cloning and expression of heparinase I gene from Flavobacterium heparinum. Proc Natl Acad Sci U S A. Apr. 15, 1993;90(8):3660-4.

Sasisekharan et al., Heparin and heparan sulfate: biosynthesis, structure and function. Curr Opin Chem Biol. Dec. 2000;4(6):626-31.

Sasisekharan et al., Heparinase inhibits neovascularization. Proc Natl Acad Sci U S A. Feb. 15, 1994;91(4):1524-8.

Seffernick et al., Melamine deaminase and atrazine chlorohydrolase: 98 percent identical but functionally different. J Bacteriol. Apr. 2001;183(8):2405-10.

Sen et al., Developments in directed evolution for improving enzyme functions. Appl Biochem Biotechnol. Dec. 2007;143(3):212-23.

Shpigel et al., Immobilization of recombinant heparinase I fused to cellulose-binding domain. Biotechnology and Bioengineering 1999, Oct; 65(1):17-23.

Shukla et al., A novel role for 3-O-sulfated heparan sulfate in herpes simplex virus 1 entry. Cell. Oct. 1, 1999;99(1):13-22.

Silva et al., Structure of heparin. Characterization of the products formed from heparin by the action of a heparinase and a heparitinase from Flavobacterium heparinum. J Biol Chem. Sep. 10, 1975;250(17):6841-6.

Tumova et al., Heparan sulfate proteoglycans on the cell surface: versatile coordinators of cellular functions. Int J Biochem Cell Biol. Mar. 2000;32(3):269-88.

Venkataraman et al., Sequencing complex polysaccharides. Science. Oct. 15, 1999;286(5439):537-42.

Vlodavsky et al., Mammalian heparanase: gene cloning, expression and function in tumor progression and metastasis. Nat Med. Jul. 1999;5(7):793-802.

Von Heijne et al., Transcending the impenetrable: how proteins come to terms with membranes. Biochim Biophys Acta. Jun. 9, 1988;947(2):307-33.

Warnick et al., Purification of an unusual-glycuronidase from flavobacteria. Biochemistry. Feb. 15, 1972;11(4):568-72.

Wishart et al., A single mutation converts a novel phosphotyrosine binding domain into a dual-specificity phosphatase. J Biol Chem. Nov. 10, 1995;270(45):26782-5.

Witkowski et al. Conversion of a beta-ketoacyl synthase to a malonyl decarboxylase by replacement of the active-site cysteine with glutamine. Biochemistry. Sep. 7, 1999;38(36):11643-50.

Xu et al., A genomic view of the human-Bacteroides thetaiotaomicron symbiosis. Science. Mar. 28, 2003;299(5615):2074-6. Alignment search ID Q89YS3 printed Jul. 11, 2005 attached.

Yang et al., Purification and characterization of heparinase from Flavobacterium heparinum. J Biol Chem. Feb. 10, 1985;260(3):1849-57.

Yates et al., 1H and 13C NMR spectral assignments of the major sequences of twelve systematically modified heparin derivatives. Carbohydr Res. Nov. 20, 1996;294:15-27.

\* cited by examiner

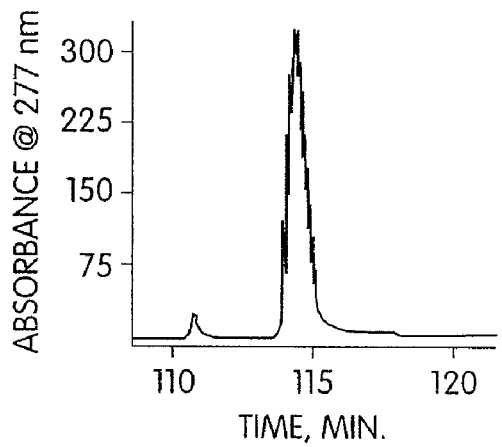
Fig. 1A
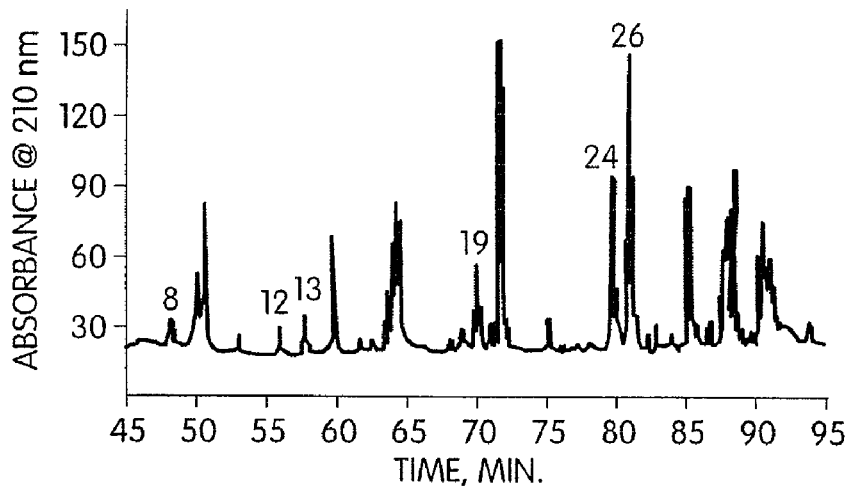
Fig. 1B
| PEAK NO. | PEPTIDE SEQUENCE |
|---|---|
| 8 | EFNKPEWFDAAK |
| 12 | PGENQFFILK |
| 13 | FTLALDTIQYVK |
| 19 | VLQRETHQGLTNESAWARGQAWGLYGYTMSYK |
| 24 | HSVGALLYNSEIDTPLNYADYYYLEALK |
| 26 | TAVIQLTRAAQTYTPGMNPRSVNPDGTVRLAPPR |
Fig. 1C

```
aagcggttttcctccgggcatcagacacaactccttttgtagttgtattttgggcatagagcgtaaggttacccg
caccaataattaatagcagtaaaaatctattcataacattttttttagttttacataatttggtttattgacaaaa
acgaatgtatagcactccaaccagaatgaatttaggtattgatcaaaatgctatcacttttgattaatcactcat
tatttcacaaaaatagatgctgtaatccaaaaaaaatcaggcattcaccaattcctaaatgaatatatccgatac
ttaaagccttacatctttacactccctaccttcatcattattaaaaaacaaaacttagatc ggaaaa taatt
atgaaatcactactcagtgcgtttgttgcgactattgcattaataggatctgcaaacgggatgacagttacgaaa
```
  1  M  K  S  L  L  S  A  F  V  A  T  I  A  L  I  G  S  A  N  G ↓ M  T  V  T  K
```
ggcaacggcgatgactggttaaagaaatcaactaaaaccgcagtaatacagttaacacgggctgcacaaacctat
```
 26  G  N  G  D  D  W  L  K  K  S  T  K  T  A  V  I  Q  L  T  R  A  A  Q  T  Y
```
acaccaggcatgaacccaaggtctgtcaatccggacgggacggtaaggctggcccctccccgcgactggaccaca
```
 51  T  P  G  M  N  P  R  S  V  N  P  D  G  T  V  R  L  A  P  P  R  D  W  T  T
```
ggttttttcccgggaacgttgtggtatggttatgaactatcggcgataaaaacctggcggccgaagccaaaaga
```
 76  G  F  F  P  G  T  L  W  Y  G  Y  E  L  S  G  D  K  N  L  A  A  E  A  K  R
```
tttaccccttgccttagatacgatacaatatgttaaagatacgcacgacctgggctttatgttgtattgttcttat
```
101  F  T  L  A  L  D  T  I  Q  Y  V  K  D  T  H  D  L  G  F  M  L  Y  C  S  Y
```
ggcaatgcctaccgtgtaaccggagacaagatttacctgaagccattagaaaacggtgcggccaatttatatgcc
```
126  G  N  A  Y  R  V  T  G  D  K  I  Y  L  K  P  L  E  N  G  A  A  N  L  Y  A
```
cgtttcaataaaaaagtaggggccatccgctcatgggatttcggacactggcaatttccggtaattatagacaac
```
151  R  F  N  K  K  V  G  A  I  R  S  W  D  F  G  H  W  Q  F  P  V  I  I  D  N
```
ctgatgaacctggagtatttatactgggcaggaaaggaattcaataagccagaatggttcgatgctgctaaaaca
```
176  L  M  N  L  E  Y  L  Y  W  A  G  K  E  F  N  K  P  E  W  F  D  A  A  K  T
```
catgcggttacgaccatgaaaaaccatttcagaaaagattatagttcttaccatgtgatcagttacgatacccctg
```
201  H  A  V  T  T  M  K  N  H  F  R  K  D  Y  S  S  Y  H  V  I  S  Y  D  T  L
```
tctggaaaagtactgcaacgtgaaacccatcagggacttaccaacgaatcggcctgggcacgggggcaagcctgg
```
226  S  G  K  V  L  Q  R  E  T  H  Q  G  L  T  N  E  S  A  W  A  R  G  Q  A  W
```
ggactttacggctataccatgagctataaggatacgaaagacaaaaaaattcatcgaacatgcagagcatatcgct
```
251  G  L  Y  G  Y  T  M  S  Y  K  D  T  K  D  K  K  F  I  E  H  A  E  H  I  A
```
gctttcatcatgaaccaccctgcaatgccggcagataaaattccactttgggactttgatgtccacaaccgcgac
```
276  A  F  I  M  N  H  P  A  M  P  A  D  K  I  P  L  W  D  F  D  V  H  N  R  D
```
aggtcgccaagggatgcttctgctgctgcagtaattgcttcagccctgctagacctgagcacgcaggtaaaagat
```
301  R  S  P  R  D  A  S  A  A  A  V  I  A  S  A  L  L  D  L  S  T  Q  V  K  D
```
ggtcagaaatatttttaaatttgccgaggatatcctgaaaacattgtcatcagatgaatacctggcgaaacccggc
```
326  G  Q  K  Y  F  K  F  A  E  D  I  L  K  T  L  S  S  D  E  Y  L  A  K  P  G
```
gagaaccagttttttatattgaaacatagtgtaggtgcattgctgtacaattcggaaatcgatacacctttgaat
```
351  E  N  Q  F  F  L  K  H  S  V  G  A  L  L  Y  N  S  E  I  D  T  P  F  N
```
tatgccgactattactatctggaggctttaaaacgctatgcagagattaaaaaaattgacctgaaaacaattaat
```
376  Y  A  D  Y  Y  Y  L  E  A  L  K  R  Y  A  E  I  K  K  I  D  L  K  T  I  N
```
cagtctaattttaaaccaacagcattataccaaaacagcaaaggctaccagggttggtagcctttgctgttttg
```
401  Q  S  STOP
```
atagttttaaaagaatttaaatcagtattgaaacattttggcagggattatttttaatttgttgaacaagaatt
aagaataaaat
```

Fig. 3

```
                       1        10         20         30         40         50         60
F. heparinum D4,5   MKSLLSAFVATIALIGSANGMTVTKGNGDEWLKKSTKTAVIQLTRAAQTYTPGMNRRSVN
     Bacillus sp.   ---------------------------------MWQQAIGDALGITAR----NLKKFG-DRFPHVSD
    S. pneumoniae   ---------------------------------MMWKQAMTDVAEKTLT----NLKRFN-GRFPHVSE
       S. pyogenes   -----MIKKVTIEKIKSPERFLEVPLITKEEVGQAIDKVIRQLELNLDYFK-EDFPTPAT
        A. bisporus   --MARPLKTIALEPIKQPERFTKEDFISQEDITQALDLALKQVRLNMDYFK-EDFPTPAT
     B. halodurans   --STHLSNMKAVVAEGFLAPSVLAATVPNELFSSLVPQKILATFNDLPNPT--QVFQYTD
         consensus   -------------i--i-----------m--qe-it-ale--lrql--nl--f---d-fP--sd 61        70         80         90        100        110
F. heparinum D4,5   P-DGTVRLAPPRDWITGFPGTIWYG---YELSGDKNLAAEAKRFTLALDT---IQYV--
     Bacillus sp.   G-SNKYVLNDNTDWLDGFWSGILWLC---YEYTGDEQYREGAVRTVASFRERLDRFEN--
    S. pneumoniae   D-GEHYELNNNNEWINGFWSGILWLC---YEYTNDPAFRQAAASTVRSFQQRMEQNLE--
       S. pyogenes   F-DNVYPIMDNTEWINGFWTGELWLA---YEYSQQDAFKNIAHKNVLSFLDRVNKRVE--
        A. bisporus   K-DNQYAIMDNTEWINAFWTGCLWLA---YEYSGDDAIKALAQANDLSFLDRVTRDIE--
     B. halodurans   QRAGDWQYFNPNTWLSGFFPSTLYALNTRRTLCGATSRNGIGIANWLELGREASRALIET
         consensus   --dn-y-l-dnteWTngFwsg-Lwla---yeysgdeayraia-rnvlsf-erl-r-le--

120        130        140        150        160
F. heparinum D4,5   --KDTHDLGFMLYCSYGNAYRVTGDKIYLKPLENGAANIYAFFNKKVGAIRSWDFG---H
     Bacillus sp.   --LDHHDIGFLYSLSAKAQWISKDESARKLALDAADVLMRRWRADAGIIQAWGPKGDPE
    S. pneumoniae   --LDHHDIGFLYSLSSKAQWILERDERAKQLTIEAADVLMKEWREKIELFQAWGPEGDLS
       S. pyogenes   --LDHHDLGFLYTPSCMAEYKINGDGEAREATLKAADKLIERYQEKGGFIQAWGDLGKKE
        A. bisporus   --LDHHDLGFLYTPSCMAEWKLLRTPESREAALKAADKLVQRYQDKGGFIQAWGELGKKE
     B. halodurans   KNSQGHDVCELSFRPFVEELAVNPNSETAVTAINSFAKLLANERPNPTVGCTRSWDAP---D
         consensus   --ldhHDlGFlysps--a-w-v-kde-ar-a-l-aAdvLm-Rwqek-g-iqaWg--g--e 170        180        190        200        210        220
F. heparinum D4,5   WQFPVILDNLMNLEYDYWAGKEFNKPEWFDAAKTHAVTTMKNHFRKDYSSYHVISYDTLS
     Bacillus sp.   NGGRILVDCLLNLPLLLWAGEQTGDPEYRRVAEAHALKSRRFLVRGDDSSVHTFYFDPEN
    S. pneumoniae   NGGRILVDCLMNLPLLFWASEVTGNPDYREAAIIRADKTRRFLVRGDDSTIHTFYFNQET
       S. pyogenes   H-VRLLIDCLLNLQLLFFAYQETGDQKYYDIAESHFYASANNVIRDDASSFHTFYFDPET
        A. bisporus   D-VRLLIDCLLNLQLLFFASQETGDNRYRPDMAINHFYASANHVIRDDASAYHTFYFDPET
     B. halodurans   PDFQVLIDNMMNLEVLFPHSAELTNNDTLRTLGKKHADTTMINHLRQDGGTWHVLHYNTFY
         consensus   --yriIiDcllNl-lLfwageetgdpeyrdva--Ha---s-rnliR-DassyHtfyfdpet 230        240        250        260        270        280
F. heparinum D4,5   GKVLQREIHQGLTNESAWARGQAWGLKGYTMSYKDTKDKKFIEHAEHIAAFIMNHPAMPA
     Bacillus sp.   GNAIRGGTHQGNTDGSTWTRGAWGINGFALNSRYLGNADLLETAKRMARHFLAR--VPE
    S. pneumoniae   GEALRGGTHQGYEDGSTWSRGQAWAINGFATAYRYTGNERYLETAKRTAKYFIEN--LPA
       S. pyogenes   QPFKGVIROGYSDDSCIARGQSWGMVIGIPLIYRHLKDESCFDLFKGVTNYFLNR--LPK
        A. bisporus   GDPVKGVTROGYSDDSAVARGQAWGIVGIPLIYRELKEPELIQLFKGMTHYFLNR--LPK
     B. halodurans   GAVTAKRIAQGFADSSTWSRGQAWGIVGYATMEKLTGKTEYRDTAVRLADYFLDH--IPN
         consensus   G--irg-ThQGytddStWaRGQaWgiYGfaltyry--d-dyletakrma-yflnr--lP- 290        300        310        320        330        340
F. heparinum D4,5   DKIPLWIRDVHNRDRSPRDASAAAVIASALQDLSTQWKD---GQKVFKFAEDILKTLSSD
     Bacillus sp.   DGVVYWDFEVPQEPSSYRDSSASAITACGLLELASQLDESDPERQRFIDAAKTTVIALRD
    S. pneumoniae   YVAYWDFNAPITPDTKRDSSASAIASCGILELLSHLQETDPDKAFQQSVQKQMISLVE
       S. pyogenes   DHVSYWDLIFNDGSDQSRDSSATAIAVCGIHEMLKHLPEVDADKDIYKHAMHAMLRSLIE
        A. bisporus   DQVSYWDLIFGDGSEQSRDSSATAIAVCGIHEMLKTLPPDHDPDKKTYEAAMHSMLRALIK
     B. halodurans   DGIVPWDFNAP---SPKPADSSAATTAANLLLSQLETTPSLKEKFSNAAIELLEKITEL
         consensus   D-v-yWDf--p--sds-rDsSAsaiaacgllells-l-e-dpdkkff--av--mvt-lvd 350        360        370        380        390        400
F. heparinum D4,5   EYLAKPGENQFFLKHSVGALLYNSEIDTPLNYAYVLEALLKRYAEIKKIDLKTINQS
     Bacillus sp.   GYAERDDGEAEGFIKRGSYHVRGGISPDDYTIWGDYVYLEALLERGVTGYWYERGR-
    S. pneumoniae   NYASEKD--AQGLLKRGSYSVRIGHAPDDYVIWGDYFYTEAIDMRLEKLRNGYWYEGK--
       S. pyogenes   HYANDQFTPGGTSLLHGVYSWHSGKGVDEGNIWGDYYLEALIRFYKDWNLYW------
        A. bisporus   DYANKDLKPGAPLLLHGVYSWHSGKGVDEGNIWGDYYLEALLRFYKDWNPYW------
     B. halodurans   AWNPS----WQSLLSNGTVNAPARNQLTG-TVYGDYFYKAGNELISMGLASCT-----
         consensus   -ya-r----a--llrhgvysv--g-avdd--iwgDYyyleAllrl-kl-ngyw-----
```

DELTA 4,5 GLYCURONIDASE COMPOSITIONS AND METHODS RELATED THERETO

RELATED APPLICATIONS

This application is a continuation of U.S. application Ser. No. 11/402,491 filed Apr. 11, 2006, allowed, which is a divisional of U.S. application Ser. No. 10/429,921 filed on May 5, 2003, pending, which claims priority under 35 U.S.C. §119 from U.S. provisional application Ser. No. 60/377,488 filed May 3, 2002, the entire contents of each of which are incorporated herein by reference.

GOVERNMENT SUPPORT

This invention was made with Government Support under Grant No. R01 GM57073, awarded by the National Institutes of Health. The Government has certain rights in this invention.

FIELD OF THE INVENTION

The invention relates to Δ4, 5 glycuronidase and uses thereof. In particular, the invention relates to substantially pure Δ4, 5 glycuronidase which is useful for a variety of purposes, including analysis of glycosaminoglycans (GAGs), sequencing, identifying, quantifying and purifying glycosaminoglycans present in a sample, removing glycosaminoglycans, such as heparin, from a solution and inhibiting angiogenesis, controlling coagulation, etc. The invention also relates to methods of treating cancer and inhibiting cellular proliferation and/or metastasis using Δ4, 5 glycuronidase and/or GAG fragments produced by enzymatic cleavage with Δ4, 5 glycuronidase.

BACKGROUND OF THE INVENTION

Glycosaminoglycans (GAGs) are linear, acidic polysaccharides that exist ubiquitously in nature as residents of the extracellular matrix and at the cell surface of many different organisms of divergent phylogeny [Habuchi, O. (2000) *Biochim Biophys Acta* 1474, 115-27; Sasisekharan, R., Bulmer, M., Moremen, K. W., Cooney, C. L., and Langer, R. (1993) *Proc Natl Acad Sci USA* 90, 3660-4]. In addition to a structural role, GAGs act as critical modulators of a number of biochemical signaling events [Tumova, S., Woods, A., and Couchman, J. R. (2000) *Int J Biochem Cell Biol* 32, 269-88] requisite for cell growth and differentiation, cell adhesion and migration, and tissue morphogenesis.

Heparan sulfate like glycosaminoglycans (GAGS or HSGAGs) are present both at the cell surface and in the extracellular matrix. Heparin-like glycosaminoglycans are important components of the extracellular matrix that are believed to regulate a wide variety of cellular activities including invasion, migration, proliferation and adhesion (Khodapkar, et al. 1998; Woods, et al., 1998). HSGAGs accomplish some of these functions by binding to and regulating the biological activities of diverse molecules, including growth factors, morphogens, enzymes, extracellular proteins. HSGAGs are a group of complex polysaccharides that are variable in length, consisting of a disaccharide repeat unit composed of glucosamine and an uronic acid (either iduronic or glucuronic acid). The high degree of complexity for HSGAGs arises not only from their polydispersity and the possibility of two different uronic acid components, but also from differential modification at four positions of the disaccharide unit. Three positions, viz., C2 of the uronic acid and the C3, C6 positions of the glucosamine can be O-sulfated. In addition, C2 of the glucosamine can be N-acetylated or N-sulfated. Together, these modifications could theoretically lead to 32 possible disaccharide units, making HSGAGs potentially more information dense than either DNA (4 bases) or proteins (20 amino acids). It is this enormity of possible structural variants that allows HSGAGs to be involved in a large number of diverse biological processes, including angiogenesis (Sasisekharan, R., Moses, M. A., Nugent, M. A., Cooney, C. L. & Langer, R. (1994) *Proc Natl Acad Sci USA*, 1524-8.), embryogenesis (Binari, R. et al (1997) *Development*, 2623-32; Tsuda, M., et al. (1999) *Nature*, 276-80.; and Lin, X., et al (1999) *Development*, 3715-23.) and the formation of β-fibrils in Alzheimer's disease (McLaurin, J., et al (1999) *Eur J Biochem*, 1101-10. and Lindahl, B., et al (1999) *J Biol Chem*, 30631-5).

One specific example of an HSGAG is heparin. Heparin, a highly sulphated HSGAG produced by mast cells, is a widely used clinical anticoagulant, and is one of the first biopolymeric drugs and one of the few carbohydrate drugs. Heparin primarily elicits its effect through two mechanisms, both of which involve binding of antithrombin III (AT-III) to a specific pentasaccharide sequence, $H_{NAc/S,6S}GH_{NS,3S,6S}I_{2S}H_{NS,6S}$ contained within the polymer. HSGAGs have also emerged as key players in a range of biological processes that range from angiogenesis [Folkman, J., Taylor, S., and Spillberg, C. (1983) *Ciba Found Symp* 100, 132-49] and cancer biology [Blackhall, F. H., Merry, C. L., Davies, E. J., and Jayson, G. C. (2001) *Br J Cancer* 85, 1094-8] to microbial pathogenesis [Shukla, et al (1999) *Cell* 99, 13-22]. HSGAGs have also recently been shown to play a fundamental role in multiple aspects of development [Perrimon, N. and Bernfield, M. (2000) *Nature* 404, 725-8]. The ability of HSGAGs to orchestrate multiple biological events is again likely a consequence of its structural complexity and information density [Sasisekharan, R. and Venkataraman, G. (2000) *Curr Opin Chem Biol* 4, 626-31].

Although the structure and chemistry of HSGAGs are fairly well understood, information on how specific HSGAG sequences modulate different biological processes has proven harder to obtain. Determination of these HSGAG sequence has been technically challenging. HSGAGs are naturally present in very limited quantities, which, unlike other biopolymers such as proteins and nucleic acids, cannot be readily amplified. Second, due to their highly charged character and structural heterogeneity, HSGAGs are not easily isolated from biological sources in a highly purified state. Additionally, the lack of sequence-specific tools to cleave HSGAGs in a manner analogous to DNA sequencing or restriction mapping has made sequencing a challenge.

Recently, in an effort to develop an understanding of HSGAG structure, focus has been placed on the cloning and characterization of the enzymes involved in HSGAG biosynthesis. Another, strategy for elucidating the structure of HSGAGs has been to employ specific HSGAG degradation procedures, including chemical or enzymatic cleavage, in conjunction with analytical methodologies, including gel electrophoresis or HPLC, to sequence HSGAGs. Recently, we have introduced a sequencing procedure that couples a bioinformatics framework with mass spectrometric and capillary electrophoretic procedures to sequence rapidly biologically important HSGAGs, including saccharide sequences involved in modulating anticoagulation. The sequencing methodology uses chemical and enzymatic tools to modify or degrade an unknown glycosaminoglycan polymer in a sequence-specific manner. (Venkataraman, G., et al., *Science*, 286, 537-542 (1999), and U.S. patent application Ser. Nos. 09/557,997 and 09/558,137, both filed on Apr. 24, 2000, having common inventorship).

SUMMARY OF THE INVENTION

Δ4, 5 glycuronidase has been cloned from the *F. heparinum* genome and its subsequent recombinant expression in *E. coli* as a soluble, highly active enzyme has been accomplished. Thus, in one aspect the present invention provides for a substantially pure Δ4,5 glycuronidase. In one embodiment of the invention the substantially pure Δ4,5 glycuronidase is a recombinantly produced glycuronidase. Recombinant expression may be accomplished in one embodiment with an expression vector. An expression vector may be a nucleic acid for SEQ ID NO:2, optionally operably linked to a promoter. In another embodiment the expression vector may be a nucleic acid for SEQ ID NO:4 or a variant thereof also optionally linked to a promoter. In one embodiment the substantially pure Δ4,5 glycuronidase is produced using a host cell comprising the expression vector. In another embodiment the substantially pure Δ4,5 glycuronidase is a synthetic glycuronidase.

In another aspect the glycuronidase of the invention is a polypeptide having an amino acid sequence of SEQ ID NO:1, or a functional variant thereof. In yet another aspect the polypeptide has an amino acid sequence of SEQ ID NO:3, or a functional variant thereof.

In yet another aspect of the invention the polypeptide of the Δ4,5 glycuronidase is an isolated polypeptide. The isolated polypeptide in some embodiments is set forth in SEQ ID NO:1 or is a functional variant thereof. In other embodiments the isolated polypeptide is set forth in SEQ ID NO:3 or a functional variant thereof.

In one aspect, the invention is a composition comprising, an isolated Δ4,5 unsaturated glycuronidase having a higher specific activity than native glycuronidase. In some embodiments, the specific activity is at least about 60 picomoles of substrate hydrolyzed per minute per picomole of enzyme. In one embodiment the Δ4,5 glycuronidase has a specific activity that is about 2 fold higher than the native enzyme. In another embodiment the Δ4,5 glycuronidase has a specific activity that is about 3 fold higher. The specific activity of the Δ4,5 glycuronidase in other embodiments may be about 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or any integer therebetween fold higher than the activity of the native enzyme.

In yet another aspect of the invention an isolated nucleic acid molecule is provided. The nucleic acid is (a) nucleic acid molecules which hybridize under stringent conditions to a nucleic acid molecule having a nucleotide sequence set forth as SEQ ID NO:2 or SEQ ID NO:4, and which code for Δ4,5 unsaturated glycuronidase having an amino acid sequence set forth as SEQ ID NO:1 or SEQ ID NO:3, respectively, (b) nucleic acid molecules that differ from the nucleic acid molecules of (a) in codon sequence due to degeneracy of the genetic code, or (c) complements of (a) or (b). In one embodiment the isolated nucleic acid molecule codes for SEQ ID NO:1. In another embodiment the isolated nucleic acid molecule comprises the nucleotide sequence set forth as SEQ ID NO:2. In still other embodiments the isolated nucleic acid molecule codes for SEQ ID NO:3 and in yet other embodiments the isolated nucleic acid molecule comprises the nucleotide sequence set forth as SEQ ID NO:4.

Pharmaceutical compositions of any of the compositions or vectors described herein are also encompassed in the invention.

In other aspects the invention relates to a method of cleaving a glycosaminoglycan with a Δ4,5 unsaturated glycuronidase. The method may be performed by contacting a glycosaminoglycan with the glycuronidase in an effective amount to cleave the glycosaminoglycan. In one embodiment the invention is a glycosaminoglycan prepared according to this method.

In other aspects the invention also provides a method of cleaving a glycosaminoglycan comprised of at least one disaccharide unit. The method may be performed by contacting the glycosaminoglycan with a glycuronidase of the invention in an effective amount to cleave the glycosaminoglycan. In some embodiments the glycosaminoglycan is a long chain saccharide. In other embodiments the glycosaminoglycan does not contain a 2-O sulfated uronidate or it does not contain N-substituted glycosamine. In yet another embodiment the glycosaminoglycan is 6-O sulfated. The disaccharide units in some embodiments are $\Delta UH_{NAc}$; $\Delta UH_{NAc,6S}$; $\Delta UH_{NS,6S}$; or $\Delta UH_{NS}$. In another embodiment the invention also provides for the products of the cleavage of a glycosaminoglycan with the Δ4,5 glycuronidase. In some embodiments the glycuronidase is used to generate a LMWH.

The present invention also provides methods for the analysis of glycosaminoglycan. In one aspect the invention is a method of analyzing a glycosaminoglycan by contacting a glycosaminoglycan with the glycuronidase of the invention in an effective amount to analyze the glycosaminoglycan. In one embodiment the method is a method for identifying the presence of a particular glycosaminoglycan in a sample. In another embodiment the method is a method for determining the identity of a glycosaminoglycan in a sample. In yet another embodiment the method is a method for determining the purity of a glycosaminoglycan in a sample. In still a further embodiment the method is a method for determining the composition of a glycosaminoglycan in a sample. In another embodiment the method is a method for determining the sequence of saccharide units in a glycosaminoglycan. In other embodiments, these methods may also comprise an additional analytical technique such as mass spectrometry, gel electrophoresis, capillary electrophoresis and HPLC. In some embodiments the glycosaminoglycan is LMWH.

In other aspects the invention is a method of removing heparin from a heparin to containing fluid by contacting a heparin containing fluid with a glycuronidase of the invention in an effective amount to remove heparin from the heparin containing fluid. In one embodiment the glycuronidase is immobilized on a solid support. In another embodiment a heparinase is also provided and the heparinase is also immobilized on the solid support.

In another aspect the invention is a method of inhibiting angiogenesis by administering to a subject in need thereof an effective amount of any of the pharmaceutical preparations described herein for inhibiting angiogenesis.

In another aspect a method of treating cancer by administering to a subject in need thereof an effective amount of any of the pharmaceutical preparations described herein for treating cancer is also provided.

Yet another aspect of the invention is a method of inhibiting cellular proliferation by administering to a subject in need thereof an effective amount of any of the pharmaceutical preparations described herein for inhibiting cellular proliferation.

In another aspect a method of treating a coagulation disease by administering to a subject in need thereof a LMWH prepared using the glycuronidase of the invention.

In some embodiments of the methods of the invention the glycuronidase is used concurrently with or following treatment with heparinase.

In other aspects of the invention, the pharmaceutical compositions and therapeutic methods are provided using the Δ4,5 unsaturated glycuronidase and the cleaved GAG fragments alone or in combination.

Other aspects of the invention provide compositions that include other enzymes such as heparinase with the Δ4,5 unsaturated glycuronidase.

In other aspects a pharmaceutical preparation of a composition or vector of the invention in a pharmaceutically acceptable carrier is provided.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE FIGURES

FIG. 1 depicts the purification of Δ4, 5 glycuronidase from *Flavobacterium* and resultant proteolysis. A. Gel filtration chromatography of the purified enzyme. B. Purification of Δ4, 5 peptides by reverse phase HPLC following trypsinization of the native protein. C. Amino acid sequence of select peptides isolated in B. Peaks 8, 12, 13, 19, 24 and 26 are SEQ ID NOs: 18-23, respectively.

FIG. 3 depicts the Δ4, 5 glycuronidase gene sequence. Full-length gene was isolated using methods outlined in FIG. 2. The amino acid and nucleic acid sequences are given in SEQ ID NOS: 3 and 4, respectively. Shown here are both the coding and flanking DNA sequences. The CDS (coding sequence) of 1209 base pairs contains an ORF encoding a putative protein of 402 amino acids. Initiation and termination codons are highlighted in bold. A possible Shine-Dalgarno (SD) sequence is boxed. The presumed signal sequence is underlined and its cleavage site delimited by a vertical arrow. The Eco R1 restriction site is double-overscored. Also shown are the degenerate primer pairs (shown as arrows) used to PCR amplify DNA hybridization probes 1 and 2 as well as the relative positions of purified Δ4, 5 peptides (shaded in gray) for which direct sequence information was obtained.

DETAILED DESCRIPTION OF THE INVENTION

Figure 2A:
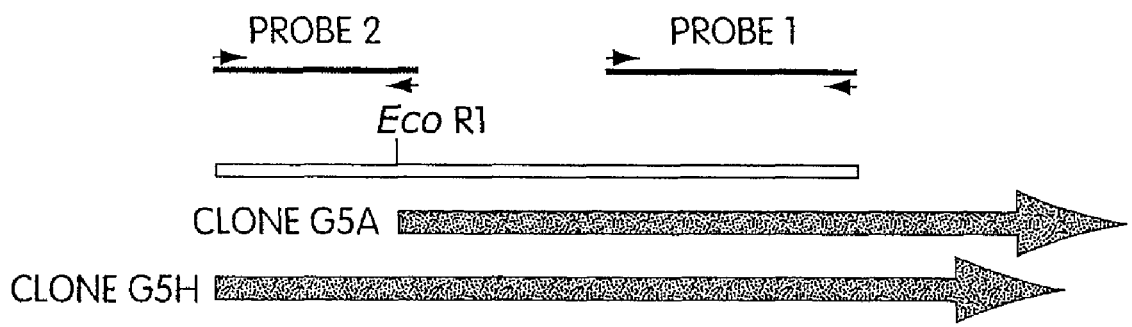
FIG. 2 provides a schematic map of Δ4, 5 genomic clones. A. Partial carboxy-terminal clones G5A and G5H (black arrows) were isolated by hybridization screening of a λZAP Flavobacterial library using probes 1 and 2, respectively. Also shown is the Eco R1 restriction site delimiting the 5' end of GSA. B. Strategy to obtain the Δ4, 5 5' terminus by Southern hybridization. Shown are the autoradiogram and its corresponding restriction map. Genomic DNA was restricted with Eco R1 alone (lane 1) or as a double digest with Hind III (lane 2), Bam H1 (lane3), or Bgl II (lane 4), respectively. DNA hybridization probe 3 used was amplified by PCR using N-terminal primers 68 and 74, both of which are 5' to the Eco R1 site. The Bgl II-Eco R1 ~1.5 kb DNA fragment (gray bar) was isolated for subcloning and DNA sequencing. C. Schematic representation of the full-length Δ4, 5 gene (1.2 kb) compiled from overlapping clones shown in A. and B.

The invention in some aspects relates to Δ4, 5 glycuronidase, substantially pure forms thereof and uses thereof. In particular the invention arose, in part, from the cloning of Δ4, 5 glycuronidase that now enables one of skill in the art to produce the enzyme in large quantities and in substantially pure form. The invention also provides another tool that may be used to determine the structure of glycosaminoglycans and to help elucidate their role in cellular processes. It has now also been discovered that substantially pure preparations of Δ4, 5 glycuronidase having higher specific activity than the enzyme produced from culture may be produced. The invention also provides for cleavage of glycosaminoglycans (GAGs) as well as for the analysis of a sample of GAGs and for their sequencing. This present invention also provides treatment and prevention methods for cancer through the control of cellular proliferation, angiogenesis and/or coagulation disorders with the enzyme and/or its cleavage products (GAG fragments).

One aspect of the invention enables one of ordinary skill in the art, in light of the present disclosure, to produce substantially pure preparations of the Δ4, 5 glycuronidase by standard technology, including recombinant technology, direct synthesis, mutagenesis, etc. For instance, using recombinant technology one may produce substantially pure preparations of the Δ4, 5 glycuronidase having the amino acid sequences of SEQ ID NO:1 or encoded by the nucleic acid sequence of SEQ ID NO:2. In other aspects of the invention substantially pure preparations of the Δ4, 5 glycuronidase having the amino acid sequences of SEQ ID NO:3 or encoded by the nucleic acid sequence of SEQ ID NO:4 can be prepared. One of skill in the art may also substitute appropriate codons to produce the desired amino acid substitutions in SEQ ID NOs:1 or 3 by standard site-directed mutagenesis techniques. One may also use any sequence which differs from the nucleic acid equivalents of SEQ ID NO:1 or 3 only due to the degeneracy of the genetic code as the starting point for site directed mutagenesis. The mutated nucleic acid sequence may then be ligated into an appropriate expression vector and expressed in a host such as *E. coli*. The resultant Δ4, 5 to glycuronidase may then be purified by techniques, including those disclosed below.

As used herein, the term "substantially pure" means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations.

As used herein, a "substantially pure Δ4,5 unsaturated glycuronidase" is a preparation of Δ4,5 unsaturated glycuronidase which has been isolated or synthesized and which is greater than about 90% free of contaminants. A contaminant is a substance with which the Δ4,5 unsaturated glycuronidase is ordinarily associated in nature that interfere with the activity of the enzyme. Preferably, the material is greater than about 91%, 92%, 93%, 94%, 95%, 96%, 97%, 98%, or even greater than about 99% free of contaminants. The degree of purity may be assessed by means known in the art. One method for assessing the purity of the material may be accomplished through the use of specific activity assays. The native Δ4,5 glycuronidase which has been described in the prior art as being isolated from *F. heparinum* has low specific activity because of impurities inherent in harvesting the enzyme from bacterial cultures of *F. heparinum*.

The invention also provides isolated polypeptides (including whole proteins and partial proteins), of Δ4, 5 glycuronidase having the amino acid sequence of SEQ ID NO:1 and functional variants thereof. Isolated polypeptides are also provided by the invention that have the amino acid sequence of SEQ ID NO:3. Polypeptides can be isolated from biological samples, and can also be expressed recombinantly in a variety of prokaryotic and eukaryotic expression systems by constructing an expression vector appropriate to the expression system, introducing the expression vector into the expression system, and isolating the recombinantly expressed protein. Polypeptides can also be synthesized chemically using well-established methods of peptide synthesis.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. Because an isolated polypeptide may be admixed with a pharmaceutically acceptable carrier in a to pharmaceutical preparation, the polypeptide may comprise only a small percentage by weight of the preparation. The polypeptide is nonetheless isolated in that it has been separated from the substances with which it may be associated in living systems, i.e., isolated from other proteins.

Thus the term "Δ4, 5 glycuronidase polypeptides" embraces variants as well as the natural Δ4, 5 glycuronidase polypeptides. As used herein, a "variant" of a Δ4, 5 glycuronidase polypeptide is a polypeptide which contains one or more modifications to the primary amino acid sequence of a naturally occurring Δ4, 5 glycuronidase polypeptide. Variants include modified Δ4, 5 glycuronidase polypeptides that do not have altered function relative to the polypeptide of the unmodified (naturally occurring) sequence. Variants also include Δ4, 5 glycuronidase polypeptides with altered function. Modifications which create a Δ4, 5 glycuronidase polypeptide variant are typically made to the nucleic acid which encodes the Δ4, 5 glycuronidase polypeptide, and can include deletions, point mutations, truncations, amino acid substitutions and addition of amino acids or non-amino acid moieties to: 1) enhance a property of a Δ4, 5 glycuronidase polypeptide, such as protein stability in an expression system or the stability of protein-protein binding; 2) provide a novel activity or property to a Δ4, 5 glycuronidase polypeptide, such as addition of a detectable moiety; or 3) to provide equivalent or better interaction with other molecules (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the Δ4, 5 glycuronidase amino acid sequence. One of skill in the art will be familiar with methods for predicting the effect on protein conformation of a change in protein sequence, and can thus "design" a variant Δ4, 5 glycuronidase polypeptide according to known methods. One example of such a method is described by Dahiyat and Mayo in Science 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

Variants can include Δ4, 5 glycuronidase polypeptides which are modified specifically to alter a feature of the polypeptide unrelated to its physiological activity. For to example, cysteine residues can be substituted or deleted to prevent unwanted disulfide linkages. Similarly, certain amino acids can be changed to enhance expression of a Δ4, 5 glycuronidase polypeptide by eliminating proteolysis by proteases in an expression system (e.g., dibasic amino acid residues in yeast expression systems in which KEX2 protease activity is present).

Mutations of a nucleic acid which encodes a Δ4, 5 glycuronidase polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant Δ4, 5 glycuronidase polypeptides) which are silent as to the amino acid sequence of the polypeptide, but which provide preferred codons for translation in a particular host. The preferred codons for translation of a nucleic acid in, e.g., E. coli, are well known to those of ordinary skill in the art. Still other mutations can be made to the noncoding sequences of a Δ4, 5 glycuronidase gene or cDNA clone to enhance expression of the polypeptide.

One type of amino acid substitution is referred to as a "conservative substitution." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants.

Methods for making amino acid substitutions, additions or deletions are well known in the art. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions, and properties of amino acids which lead to their definition as polar, non-polar or acidic.

One skilled in the art will be able to predict the effect of a substitution by using routine screening assays, preferably the biological assays described herein. Modifications of peptide properties including thermal stability, enzymatic activity, hydrophobicity, susceptibility to proteolytic degradation or the tendency to aggregate with carriers or into multimers are assayed by methods well known to the ordinarily skilled artisan. For additional detailed description of protein chemistry and structure, see Schulz, G. E. et al., Principles of Protein Structure, Springer-Verlag, New York, 1979, and Creighton, T. E., Proteins: Structure and Molecular Principles, W.H. Freeman & Co., San Francisco, 1984.

Additionally, some of the amino acid substitutions are non-conservative substitutions. In certain embodiments where the substitution is remote from the active or binding sites, the non-conservative substitutions are easily tolerated provided that they preserve a tertiary structure characteristic of, or similar to, native Δ4, 5 glycuronidase, thereby preserving the active and binding sites. Non-conservative substitutions, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain.

In another set of embodiments an isolated nucleic acid equivalent of SEQ ID NO:2 encode the substantially pure Δ4, 5 glycuronidase of the invention and functional variants thereof. In still further embodiments isolated nucleic acid equivalents of SEQ ID NO:4 are also given. According to the invention, isolated nucleic acid molecules that code for a Δ4, 5 glycuronidase polypeptide are provided and include: (a) nucleic acid molecules which hybridize under stringent conditions to a molecule selected from a group consisting of the nucleic acid equivalent of SEQ ID NO:2 or 4 and which code for a Δ4, 5 glycuronidase polypeptide or parts thereof, (b) deletions, additions and substitutions of (a) which code for a respective Δ4, 5 glycuronidase polypeptide or parts thereof, (c) nucleic acid molecules that differ from the nucleic acid molecules of (a) or (b) in codon sequence due to the degeneracy of the genetic code, and (d) complements of (a), (b) or (c).

The invention also includes degenerate nucleic acids which include alternative codons to those present in the naturally occurring materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Δ4, 5 glycuronidase polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its naturally occurring state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

One embodiment of the invention provides Δ4, 5 glycuronidase that is recombinantly produced. Such molecules may be recombinantly produced using a vector including a coding sequence operably joined to one or more regulatory sequences. As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence to may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, the term "stringent conditions" refers to parameters known to those skilled in the art. One example of stringent conditions is hybridization at 65° C. in hybridization buffer (3.5×SSC, 0.02% Ficoll, 0.02% polyvinyl pyrrolidone, 0.02% bovine serum albumin (BSA), 25 mM $NaH_2PO_4$ (pH7), 0.5% SDS, 2 mM EDTA). SSC is 0.15M sodium chloride/0.015M sodium citrate, pH7; SDS is sodium dodecylsulphate; and EDTA is ethylene diamine tetra acetic acid. There are other conditions, reagents, and so forth which can be used, which result in the same degree of stringency. A skilled artisan will be familiar with such conditions, and thus they are not given here.

The skilled artisan also is familiar with the methodology for screening cells for expression of such molecules, which then are routinely isolated, followed by isolation of the pertinent nucleic acid. Thus, homologs and alleles of the substantially pure Δ4, 5 glycuronidase of the invention, as well as nucleic acids encoding the same, may be obtained routinely, and the invention is not intended to be limited to the specific sequences disclosed. It will be understood that the skilled artisan will be able to manipulate the conditions in a manner to permit the clear identification of homologs and alleles of the Δ4, 5 glycuronidase nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least about 40% nucleotide identity and/or at least about 50% amino acid identity with the equivalents of SEQ ID Nos: 2 and 1, respectively. Homologs and alleles of the invention are also intended to encompass the nucleic acid and amino acid equivalents of SEQ ID Nos: 4 and 3, respectively. In some instances sequences will share at least about 50% nucleotide identity and/or at least about 65% amino acid identity and in still other instances sequences will share at least about 60% nucleotide identity and/or at least about 75% amino acid identity. The homology can be calculated using various, publicly available software tools developed by NCBI (Bethesda, Md.) that can be obtained through the internet (ftp:/ncbi.nlm nih gov/pub/). Exemplary tools include the BLAST system available at http://wwww.ncbi.nlm nih gov. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

In screening for Δ4, 5 glycuronidase related genes, such as homologs and alleles of Δ4, 5 glycuronidase, a Southern blot may be performed using the foregoing conditions, together with a radioactive probe. After washing the membrane to which the DNA is finally transferred, the membrane can be placed against X-ray film or a phosphoimager plate to detect the radioactive signal.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria such as *E. coli, Flavobacterium heparinum, Bacillus, Streptomyces, Pseudomonas, Salmonella, Serratia*, and the like.

To express the substantially pure Δ4, 5 glycuronidase of the invention in a to prokaryotic cell, it is desirable to operably join the nucleic acid sequence of a substantially pure Δ4, 5 glycuronidase of the invention to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ, ($P_L$ and $P_R$), the trp, recA, lacZ, lad, and gal promoters of E. coli, the α-amylase (Ulmanen et al., J. Bacteriol. 162:176-182 (1985)) and the ζ-28-specific promoters of B. subtilis (Gilman et al., Gene sequence 32:11-20 (1984)), the promoters of the bacteriophages of Bacillus (Gryczan, In: The Molecular Biology of the Bacilli, Academic Press, Inc., NY (1982)), and Streptomyces promoters (Ward et al., Mol. Gen. Genet. 203:468-478 (1986)).

Prokaryotic promoters are reviewed by Glick (J. Ind. Microbiol. 1:277-282 (1987)); Cenatiempo (Biochimie 68:505-516 (1986)); and Gottesman (Ann. Rev. Genet. 18:415-442 (1984)).

Proper expression in a prokaryotic cell also requires the presence of a ribosome binding site upstream of the encoding sequence. Such ribosome binding sites are disclosed, for example, by Gold et al. (Ann. Rev. Microbiol. 35:365-404 (1981)).

Because prokaryotic cells may not produce the Δ4, 5 glycuronidase of the invention with normal eukaryotic glycosylation, expression of the Δ4, 5 glycuronidase of the invention of the eukaryotic hosts is useful when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in Drosophila larvae. Using insect cells as hosts, the Drosophila alcohol dehydrogenase promoter can be used (Rubin, Science 240:1453-1459 (1988)). Alternatively, baculovirus vectors can be engineered to express large amounts of the Δ4, 5 glycuronidase of the invention in insect cells (Jasny, Science 238:1653 (1987); Miller et al., In: Genetic Engineering (1986), Setlow, J. K., et al., eds., Plenum, Vol. 8, pp. 277-297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals that are temperature-sensitive so that by varying the temperature, expression can be repressed or initiated, or which are subject to chemical (such as metabolite) regulation.

As discussed above, expression of the Δ4, 5 glycuronidase of the invention in eukaryotic hosts is accomplished using eukaryotic regulatory regions. Such regions will, in general, include a promoter region sufficient to direct the initiation of RNA synthesis. Preferred eukaryotic promoters include, for example, the promoter of the mouse to metallothionein I gene sequence (Hamer et al., J. Mol. Appl. Gen. 1:273-288 (1982)); the TK promoter of Herpes virus (McKnight, Cell 31:355-365 (1982)); the SV40 early promoter (Benoist et al., Nature (London) 290:304-310 (1981)); the yeast gal4 gene sequence promoter (Johnston et al., Proc. Natl. Acad. Sci. (USA) 79:6971-6975 (1982); Silver et al., Proc. Natl. Acad. Sci. (USA) 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the Δ4, 5 glycuronidase of the invention does not contain any intervening codons which are capable of encoding a methionine (i.e., AUG). The presence of such codons results either in the formation of a fusion protein (if the AUG codon is in the same reading frame as the Δ4, 5 glycuronidase of the invention coding sequence) or a frame-shift mutation (if the AUG codon is not in the same reading frame as the Δ4, 5 glycuronidase of the invention coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed, or introduced into the same cell by co-transfection. Additional elements may also be needed for optimal synthesis of the Δ4, 5 glycuronidase mRNA. These elements may include splice signals, as well as transcription promoters, enhancers, and termination signals. cDNA expression vectors incorporating such elements include those described by Okayama, Molec. Cell. Biol. 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, and πVX). Such plasmids are, for example, disclosed by Sambrook, et al. (*Molecular Cloning: A Laboratory Manual*, second edition, edited by Sambrook, Fritsch, & Maniatis, Cold Spring Harbor Laboratory, 1989)). *Bacillus* plasmids include pC194, pC221, pT127, and the like. Such plasmids are disclosed by Gryczan (In: *The Molecular Biology of the Bacilli*, Academic Press, NY (1982), pp. 307-329). Suitable *Streptomyces* plasmids include pIJ101 (Kendall et al., *J. Bacteriol.* 169:4177-4183 (1987)), and *streptomyces* bacteriophages such as φC31 (Chater et al., In: *Sixth International Symposium on Actinomycetales Biology*, Akademiai Kaido, Budapest, Hungary (1986), pp. 45-54). *Pseudomonas* plasmids are reviewed by John et al. (*Rev. Infect. Dis.* 8:693-704 (1986)), and Izaki (*Jpn. J. Bacteriol.* 33:729-742 (1978)).

Preferred eukaryotic plasmids include, for example, BPV, EBV, SV40, 2-micron circle, and the like, or their derivatives. Such plasmids are well known in the art (Botstein et al., *Miami Wntr. Symp.* 19:265-274 (1982); Broach, In: *The Molecular Biology of the Yeast Saccharomyces: Life Cycle and Inheritance*, Cold Spring Harbor Laboratory, Cold Spring Harbor, N.Y., p. 445-470 (1981); Broach, *Cell* 28:203-204 (1982); Bollon et al., *J. Clin. Hematol. Oncol.* 10:39-48 (1980); Maniatis, In: *Cell Biology: A Comprehensive Treatise*, Vol. 3, Gene Sequence Expression, Academic Press, NY, pp. 563-608 (1980)). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or insert RNA.

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. Additionally, DNA or RNA encoding the Δ4, 5 glycuronidase of the invention may be directly injected into cells or may be impelled through cell membranes after being adhered to microparticles. After the introduction of the vector, recipient cells are grown in a selective medium, which selects for the growth of vector-containing cells. Expression of the cloned gene sequence(s) results in the production of the Δ4, 5 glycuronidase of the to invention. This can take place in the transformed cells as such, or following the induction of these cells to differentiate (for example, by administration of bromodeoxyuracil to neuroblastoma cells or the like).

The present invention also provides for the use of Δ4, 5 glycuronidase as an enzymatic tool due to its substrate specificity and specific activity. In a direct and more rigorous comparison between the recombinant and native enzymes, it was found that at least some of the recombinant enzyme ($\Delta 4,5^{\Delta 20}$) possessed at least about two-fold higher and in some cases a roughly about three-fold higher specific activity relative to the native Flavobacterial enzyme when measured under identical reaction conditions. Additionally, the activity of a cloned enzyme is not compromised by its recombinant expression in *E. coli*.

The recombinant Δ4,5 glycuronidase exhibited a sharp ionic strength dependence. These results are interesting given both the ionic character of the disulfated heparin disaccharide used in the experiments described below as well as the many ionic residues present within the enzyme that may function in substrate binding and/or catalysis; many of these charged residues are conserved in structurally and functionally related enzymes. From a substrate perspective, all of the unsaturated disaccharides examined possess a negative charge (at pH 6.4) due to the C6 carboxylate of the uronic acid. It is possible that this acid acts as a critical structural determinant, especially given its proximity to the Δ4,5 bond. Charge neutralization of 6-O sulfate (e.g., in $\Delta UH_{NS,6S}$) could possibly be another contributing factor. From the enzyme perspective, the recombinant glycuronidase ($\Delta 4,5^{\Delta 20}$) does possess 47 basic residues (theoretical pI of 8.5), including R151 whose position is invariantly conserved among the different glycuronidases examined. R151 may possibly interact with the uronic acid carboxylate. At the same time, Δ4,5 also possesses 44 acidic residues. At least ten of these positions are highly conserved. Charge masking of some of these ionic residues (either acidic or basic) by increasing salt concentration might interfere with enzymatic activity. A similar observation of this ionic strength dependency has been made for the heparinases [Ernst S, et al Expression in *Escherichia coli*, purification and characterization of heparinase I from *Flavobacterium heparinum*. Biochem J. 1996 Apr. 15; 315 (pt 2): 589-97.]

A bell-shaped pH profile with a 6.4 optimum was also observed in the present invention. The 6.4 pH optimum generally agrees with results originally reported for the *F. heparinum* Δ4,5 as well as for more recent results published for an unsaturated glucuronyl to hydrolase purified from *Bacillus* sp. GL1 [Hashimoto, W., et al. (1999) *Arch Biochem Biophys* 368, 367-74]. While there are 11 histidines present within the primary sequence, three histidines (H115, H201, and H218) appear to be highly conserved. Interestingly, catalytically critical histidines also exist in all three heparin lyases [Pojasek, K., et al. (2000) *Biochemistry* 39, 4012-9] as well as chondroitin AC lyase [Huang, W., et al. (2001) *Biochemistry* 40, 2359-72] from *Flavobacterium heparinum*. While these two classes of enzymes cleave glycosaminoglycans by somewhat different mechanisms (i.e., β-elmination vs. hydrolysis), both would presumably involve acid-base catalysis, viz the imidazole.

The question of substrate specificity has now been considered from three structural perspectives: (1) the nature of the glycosidic linkage; (2) the relative sulfation pattern of the unsaturated disaccharide; and (3) the role of saccharide chain length (e.g., di-vs. tetrasaccharide). Our results indicate that for the recombinant Δ4,5 glycuronidase, there is an unambiguous preference for the 1→4 linkage over the 1→3 linkage making heparin rather than chondroitin/dermatan and/or hyaluronan the best substrate. It should be noted, however, that while this linkage position is important, it is not absolute. Both chondroitin and hyaluronan Δ4,5 disaccharides were hydrolyzed, albeit at much slower rates and using higher enzyme concentrations than were required to hydrolyze heparin disaccharides.

We also present a kinetic pattern of the Δ4,5 glycuronidase with regard to the specific sulfation within a heparin disaccharide. First and foremost, we find that unsaturated saccharides containing a 2-O-sulfated uronidate ($\Delta U_{2S}$) at the non-reducing end are in general not cleaved by the Δ4,5 glycuronidase. Furthermore, the inability of a 2-O-sulfated disaccharide to competitively inhibit the hydrolysis of non 2-O-containing disaccharide substrates (such as $\Delta UH_{NAc}$) further suggests that the presence of a 2-O sulfate precludes binding of this saccharide to the enzyme.

In considering the effect of specific sulfate groups present on the glucosamine, the enzyme may be loosely summarized as having a graded preference for 6-O-sulfation but a clear selection against unsubstituted or sulfated amines. This hierarchy is not an absolute distinction given the fact that all the non 2-O-containing heparin disaccharides examined were cleaved by the enzyme. Instead, it is based on relative kinetic parameters. This apparent substrate discrimination at the N and 6 positions of the glucosamine appears to be somewhat contextual, especially in the case of 6-O-sulfation. That is, while 6-O sulfation may bestow a favorable selectivity to a saccharide substrate, this positive effect may be offset by the presence of a deacetylated amine (e.g., $\Delta UH_{NAc6S}$ vs. $\Delta UH_{NH26S}$ or $\Delta UH_{NS,6S}$).

The structural preference the $\Delta 4,5$ demonstrates against 2-O-sulfated uronidates along with a so-called "N-position" discrimination for the glucosamine may be exploited for use of the glycuronidase as an analytical tool for the compositional analyses of glycosaminoglycans. We were able to predict the extent and relative rates by which specific disaccharide "peaks" would disappear (i.e., due to the glycuronidase-dependent loss of absorbance at 232 nm.), based entirely on our kinetically defined substrate specificity determinations described in the Examples below. All 2-O-sulfate containing disaccharides tested were refractory to hydrolysis by the $\Delta 4,5$ glycuronidase. On the other hand, the remaining disaccharides were hydrolyzed in a time-dependent fashion that corresponded to their relative substrate specificities (i.e., $\Delta UH_{NAc6S} > \Delta UH_{NS,6S} > \Delta UH_{NS}$).

From this experiment, another important and surprising observation was made, namely that the $\Delta 4,5$ glycuronidase also hydrolyzes $\Delta 4,5$ unsaturated tetrasaccharides. It is also very interesting to note that this particular tetrasaccharide is as good of a substrate as the disaccharide $\Delta UH_{NS}$. This observation may argue against a substrate discrimination used by the enzyme that is negatively based on increasing molecular weight as was first reported [Hovingh, P. and Linker, A. (1977) *Biochem J* 165, 287-93].

Therefore, the invention also provides for the cleavage of glycosaminoglycans using the substantially pure $\Delta 4,5$ glycuronidase described herein. The $\Delta 4,5$ glycuronidase of the invention may be used to specifically cleave an HSGAG by contacting the HSGAG substrate with the $\Delta 4,5$ glycuronidase of the invention. The invention is useful in a variety of in vitro, in vivo and ex vivo methods in which it is useful to cleave HSGAGs.

As used herein the terms "HSGAG", "GAG", and "glycosaminoglycans" are used interchangeably to refer to a family of molecules having heparin-like/heparan sulfate-like structures and properties. These molecules include but are not limited to low molecular weight heparin (LMWH), heparin, biotechnologically prepared heparin, chemically modified heparin, synthetic heparin, and heparan sulfate. The term "biotechnological heparin" encompasses heparin that is prepared from natural sources of polysaccharides which have been chemically modified and is described for example in Razi et al., Bioche. J. 1995 Jul. 15; 309 (Pt 2): 465-72. Chemically modified heparin is described in Yates et al., Carbohydrate Res (1996) November 20; 294:15-27, and is known to those of skill in the art. Synthetic heparin is well known to those of skill in the art and is described in Petitou, M. et al., Bioorg Med Chem Lett. (1999) Apr. 19; 9(8):1161-6.

Analysis of a sample of glycosaminoglycans is also possible with $\Delta 4,5$ glycuronidase alone or in conjunction with other enzymes. Other HSGAG degrading enzymes include but are not limited to heparinase-I, heparinase-II, heparinase-III, heparinase-IV, D-glucuronidase and L-iduronidase, modified versions of heparinases, variants and functionally active fragments thereof.

The methods that may be used to test the specific activity of $\Delta 4,5$ glycuronidase of the present invention are known in the art, e.g., those described in the Examples. These methods may also be used to assess the function of variants and functionally active fragments of $\Delta 4,5$ glycuronidase. The $k_{cat}$ value may be determined using any enzymatic activity assay to assess the activity of a $\Delta 4,5$ glycuronidase enzyme. Several such assays are well-known in the art. For instance, an assay for measuring $k_{cat}$ is described in (Ernst, S. E., Venkataraman, G., Winkler, S., Godavarti, R., Langer, R., Cooney, C. and Sasisekharan. R. (1996) Biochem. J. 315, 589-597. The "native $\Delta 4,5$ glycuronidase $k_{cat}$ value" is the measure of enzymatic activity of the native $\Delta 4,5$ glycuronidase obtained from cell lysates of *F. heparinum* also described in the Examples below. Therefore, based on the disclosure provided herein, those of ordinary skill in the art will be able to identify other $\Delta 4,5$ glycuronidase molecules having altered enzymatic activity with respect to the naturally occurring $\Delta 4,5$ glycuronidase molecule such as functional variants.

The term "specific activity" as used herein refers to the enzymatic activity of a preparation of $\Delta 4,5$ glycuronidase. In general, it is preferred that the substantially pure and/or isolated $\Delta 4,5$ glycuronidase preparations of the invention have a specific activity of at least about 60 picomoles of substrate hydrolized per minute per picomole of enzyme. This generally corresponds to a $k_{cat}$ of at least about 10 per second for the enzyme using a substrate such as heparin disaccharide $\Delta UH_{NAc}$.

Due to the activity of $\Delta 4,5$ glycuronidase on glycosaminoglycans, the product profile produced by a $\Delta 4,5$ glycuronidase may be determined by any method known in the art for examining the type or quantity of degradation product produced by $\Delta 4,5$ glycuronidase alone or in combination with other enzymes. One of skill in the art will also recognize that the $\Delta 4,5$ glycuronidase may also be used to assess the purity of glycosaminoglycans in a sample. One preferred method for determining the type and quantity of product is described in Rhomberg, A. J. et al., *PNAS*, v. 95, p. 4176-4181, (April 1998), which is hereby incorporated in its entirety by reference. The method disclosed in the Rhomberg reference utilizes a combination of mass spectrometry and capillary electrophoretic techniques to identify the enzymatic products produced by heparinase. The Rhomberg study utilizes heparinase to degrade HSGAGs to produce HSGAG oligosaccharides. MALDI (Matrix-Assisted Laser Desorption Ionization) mass spectrometry can be used for the identification and semiquantitative measurement of substrates, enzymes, and end products in the enzymatic reaction. The capillary electrophoresis technique separates the products to resolve even small differences amongst the products and is applied in combination with mass spectrometry to quantitate the products produced. Capillary electrophoresis may even resolve the difference between a disaccharide and its semicarbazone derivative. Detailed methods for sequencing polysaccharides and other polymers are disclosed in co-pending U.S. patent application Ser. Nos. 09/557,997 and 09/558,137, both filed on Apr. 24, 2000 and having common inventorship. The entire contents of both applications are hereby incorporated by reference.

For example, the method is performed by enzymatic digestion, followed by mass spectrometry and capillary electrophoresis. The enzymatic assays can be performed in a variety of manners, as long as the assays are performed identically on the $\Delta 4,5$ glycuronidase, so that the results may be compared. In the example described in the Rhomberg reference, enzymatic reactions are performed by adding 1 mL of enzyme solution to 5 mL of substrate solution. The digestion is then carried out at room temperature (22° C.), and the reaction is stopped at various time points by removing 0.5 mL of the reaction mixture and adding it to 4.5 mL of a MALDI matrix solution, such as caffeic acid (approximately 12 mg/mL) and 70% acetonitrile/water. The reaction mixture is then subjected to MALDI mass spectrometry. The MALDI surface is prepared by the method of Xiang and Beavis (Xiang and Beavis (1994) *Rapid. Commun. Mass. Spectrom.* 8, 199-204). A two-fold lower access of basic peptide $(Arg/Gly)_{15}$ is premixed with matrix before being added to the oligosaccharide solution. A 1 mL aliquot of sample/matrix mixture containing 1-3 picomoles of oligosaccharide is deposited on the surface. After crystallization occurs (typically within 60 seconds), excess liquid is rinsed off with water. MALDI mass spectrometry spectra is then acquired in the linear mode by using a PerSeptive Biosystems (Framingham, Mass.) Voyager Elite reflectron time-of-flight instrument fitted with a 337 nanometer nitrogen laser. Delayed extraction is used to increase resolution (22 kV, grid at 93%, guidewire at 0.15%, pulse delay 150 ns, low mass gate at 1,000, 128 shots averaged). Mass spectra are calibrated externally by using the signals for proteinated $(Arg/Gly)_{15}$ and its complex with the oligosaccharide.

Capillary electrophoresis may then be performed on a Hewlett-Packard$^{3D}$ CE unit by using uncoated fused silica capillaries (internal diameter 75 micrometers, outer diameter 363 micrometers, $1_{det}$ 72.1 cm, and $1_{tot}$ 85 cm). Analytes are monitored by using UV detection at 230 nm and an extended light path cell (Hewlett-Packard). The electrolyte is a solution of 10 mL dextran sulfate and 50 millimolar Tris/phosphoric acid (pH2.5). Dextran sulfate is used to suppress nonspecific interactions of the heparin oligosaccharides with a silica wall. Separations are carried out at 30 kV with the anode at the detector side (reversed polarity). A mixture of a 1/5-naphtalenedisulfonic acid and 2-naphtalenesulfonic acid (10 micromolar each) is used as an internal standard.

Other methods for assessing the product profile may also be utilized. For instance, other methods include methods which rely on parameters such as viscosity (Jandik, K. A., Gu, K. and Linhardt, R. J., (1994), *Glycobiology,* 4:284-296) or total UV absorbance (Ernst, S. et al., (1996), *Biochem. J.,* 315:589-597) or mass spectrometry or capillary electrophoresis alone.

The Δ4,5 glycuronidase molecules of the invention are also useful as tools for sequencing HSGAGs. Detailed methods for sequencing polysaccharides and other polymers are disclosed in co-pending U.S. patent application Ser. Nos. 09/557,997 and 09/558,137, both filed on Apr. 24, 2000 and having common inventorship. These methods utilize tools such as heparinases in the sequencing process. The Δ4,5 glycuronidase of the invention is useful as such a tool.

One of ordinary skill in the art, in light of the present disclosure, is enabled to produce substantially pure preparations of HSGAG and/or GAG fragment compositions utilizing the Δ4, 5 glycuronidase molecules alone or in conjunction with other enzymes. These GAG fragments have many therapeutic utilities. The glycuronidase molecules and/or GAG fragments can be used for the treatment of any type of condition in which GAG fragment therapy has been identified as a useful therapy, e.g., preventing coagulation, inhibiting angiogenesis, inhibiting proliferation. The GAG fragment preparations are to prepared from HSGAG sources. A "HSGAG source" as used herein refers to heparin-like/heparan sulfate-like glycosaminoglycan composition which can be manipulated to produce GAG fragments using standard technology, including enzymatic degradation etc. As described above, HSGAGs include but are not limited to isolated heparin, chemically modified heparin, biotechnology prepared heparin, synthetic heparin, heparan sulfate, and LMWH. Thus HSGAGs can be isolated from natural sources, prepared by direct synthesis, mutagenesis, etc.

Thus, the methods of the invention enable one of skill in the art to prepare or identify an appropriate composition of GAG fragments, depending on the subject and the disorder being treated. These compositions of GAG fragments may be used alone or in combination with the Δ4,5 glycuronidase and/or other enzymes. Likewise Δ4, 5 glycuronidase and/or other enzymes may also be used to produce GAG fragments in vivo.

The compositions of the invention can be used for the treatment of any type of condition in which GAG fragment therapy has been identified as a useful therapy. Thus, the invention is useful in a variety of in vitro, in vivo and ex vivo methods in which therapies are useful. For instance, it is known that GAG fragments are useful for preventing coagulation, inhibiting cancer cell growth and metastasis, preventing angiogenesis, preventing neovascularization, preventing psoriasis. The GAG fragment compositions may also be used in in vitro assays, such as a quality control sample.

Each of these disorders is well-known in the art and is described, for instance, in Harrison's Principles of Internal Medicine (McGraw Hill, Inc., New York), which is incorporated by reference.

In one embodiment the preparations of the invention are used for inhibiting angiogenesis. An effective amount for inhibiting angiogenesis of the GAG fragment preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to endothelial cell growth factors. The inhibition of angiogenesis can cause tumor regression in animal models, suggesting a use as a therapeutic anticancer to agent. An effective amount for inhibiting angiogenesis is an amount of GAG fragment preparation which is sufficient to diminish the number of blood vessels growing into a tumor. This amount can be assessed in an animal model of tumors and angiogenesis, many of which are known in the art.

The Δ4, 5 glycuronidase is, in some embodiments, immobilized on a support. The glycuronidase may be immobilized to any type of support but if the support is to be used in vivo or ex vivo it is desired that the support is sterile and biocompatible. A biocompatible support is one which would not cause an immune or other type of damaging reaction when used in a subject. The Δ4, 5 glycuronidase may be immobilized by any method known in the art. Many methods are known for immobilizing proteins to supports. A "solid support" as used herein refers to any solid material to which a polypeptide can be immobilized.

Solid supports, for example, include but are not limited to membranes, e.g., natural and modified celluloses such as nitrocellulose or nylon, Sepharose, Agarose, glass, polystyrene, polypropylene, polyethylene, dextran, amylases, polyacrylamides, polyvinylidene difluoride, other agaroses, and magnetite, including magnetic beads. The carrier can be totally insoluble or partially soluble and may have any possible structural configuration. Thus, the support may be spherical, as in a bead, or cylindrical, as in the inside surface of a test tube or microplate well, or the external surface of a rod. Alternatively, the surface may be flat such as a sheet, test strip, bottom surface of a microplate well, etc.

The Δ4, 5 glycuronidase of the invention may also be used to remove active GAGs from a GAG containing fluid. A GAG containing fluid is contacted with the Δ4, 5 glycuronidase of the invention to degrade the GAG. The method is particularly useful for the ex vivo removal of GAGs from blood. In one embodiment of the invention the Δ4, 5 glycuronidase is immobilized on a solid support as is conventional in the art. The solid support containing the immobilized Δ4, 5 glycuronidase may be used in extracorporeal medical devices (e.g. hemodialyzer, pump-oxygenator) for systemic heparinization to prevent the blood in the device from clotting. The support membrane containing immobilized Δ4, 5 glycuronidase is positioned at the end of the device to neutralize the GAG before the blood is returned to the body.

Thus, the Δ4, 5 glycuronidase molecules are useful for treating or preventing disorders associated with coagulation. A "disease associated with coagulation" as used to herein refers to a condition characterized by an interruption in the blood supply to a tissue due to a blockage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The Δ4, 5 glycuronidase or the GAG fragments generated therewith may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol;* v.25 (7 suppl), p. 10S-17S(1995)). Thrombolytic agents include, but are not limited to, plasminogen, $a_2$-antiplasmin, streptokinase, antistreplase, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin The fibrinolytic activity of tPA may be determined by any in vitro clot lysis activity known in the art, such as the purified clot lysis assay described by Carlson, et. al., *Anal. Biochem.* 168, 428-435 (1988) and its modified form described by Bennett, W. F. et al., 1991, *J. Biol. Chem.* 266(8):5191-5201, the entire contents of which are hereby incorporated by reference.

The invention compositions of the invention are useful for the same purposes as heparinases and the degradation products of heparinases (HSGAG fragments). Thus, for instance, the compositions of the invention are useful for treating and preventing cancer cell proliferation and metastasis. Thus, according to another aspect of the invention, there is provided methods for treating subjects having or at risk of having cancer.

Critically, HSGAGs (along with collagen) are key components of the cell surface-extracellular matrix (ECM) interface. While collagen-like proteins provide the necessary extracellular scaffold for cells to attach and form tissues, the complex polysaccharides fill the space created by the scaffold and act as a molecular sponge by specifically binding and regulating the biological activities of numerous signaling molecules like growth factors, cytokines etc. It has recently been recognized that cells synthesize distinct HSGAG sequences and decorate themselves with these sequences, using the extraordinary information content present in the sequences to bind specifically to many signaling molecules and thereby regulate various biological processes.

The invention also contemplates the use of therapeutic GAG fragments for the treatment and prevention of tumor cell proliferation and metastasis. A "therapeutic GAG fragment" as used herein refers to a molecule or molecules which are pieces or fragments of a GAG that have been identified or generated through the use of the Δ4, 5 glycuronidase possibly along with other naturally occurring and/or modified heparinases. In some aspects the therapeutic GAG fragments have the same structure as commercially available LMWH, but are generated using the Δ4, 5 glycuronidase.

The invention also encompasses screening assays for identifying therapeutic GAG fragments for the treatment of a tumor and for preventing metastasis. The assays are accomplished by treating a tumor or isolated tumor cells with Δ4, 5 glycuronidase and/or other naturally occurring or modified heparinases and isolating the resultant GAG fragments. Surprisingly, these GAG fragments have therapeutic activity in the prevention of tumor cell proliferation and metastasis. Thus the invention encompasses individualized to therapies, in which a tumor or portion of a tumor is isolated from a subject and used to prepare the therapeutic GAG fragments. These therapeutic fragments can be re-administered to the subject to protect the subject from further tumor cell proliferation or metastasis or from the initiation of metastasis if the tumor is not yet metastatic. Alternatively the fragments can be used in a different subject having the same type or tumor or a different type of tumor.

Therapeutic GAG fragments include GAG fragments which have therapeutic activity in that they prevent the proliferation and/or metastasis of a tumor cell. Such compounds may be generated using Δ4, 5 glycuronidase to produce therapeutic fragments or they may be synthesized de novo. Putative GAG fragments can be tested for therapeutic activity using any of the assays described herein or known in the art. Thus the therapeutic GAG fragment may be a synthetic GAG fragment generated based on the sequence of the GAG fragment identified when the tumor is contacted with Δ4, 5 glycuronidase, or having minor variations which do not interfere with the activity of the compound. Alternatively the therapeutic GAG fragment may be an isolated GAG fragment produced when the tumor is contacted with Δ4, 5 glycuronidase.

The invention is useful for treating and/or preventing tumor cell proliferation or metastasis in a subject. The terms "treat"

and "treating" tumor cell proliferation as used herein refer to inhibiting completely or partially the proliferation or metastasis of a cancer or tumor cell, as well as inhibiting any increase in the proliferation or metastasis of a cancer or tumor cell.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

A "subject at risk of having a cancer" as used herein is a subject who has a high probability of developing cancer. These subjects include, for instance, subjects having a genetic abnormality, the presence of which has been demonstrated to have a correlative to relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with a Δ4, 5 glycuronidase or degradation product thereof the subject may be able to kill the cancer cells as they develop.

Effective amounts of the Δ4, 5 glycuronidase, variant Δ4, 5 glycuronidase or therapeutic GAGs of the invention are administered to subjects in need of such treatment. Effective amounts are those amounts which will result in a desired improvement in the condition or symptoms of the condition, e.g., for cancer this is a reduction in cellular proliferation or metastasis, without causing other medically unacceptable side effects. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In some aspects of the invention the effective amount of Δ4, 5 glycuronidase or therapeutic GAG is that amount effective to prevent invasion of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties Liotta, L. A., et al., Cell 64:327-336, 1991. Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the Δ4, 5 glycuronidase compositions or degradation products thereof can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer, 1992, 52:378-383. Matrigel is a reconstituted basement membrane containing type IV collagen, laminin, heparan sulfate proteoglycans such as perlecan, which bind to and localize bFGF, vitronectin as well as transforming growth factor-β (TGF-β) urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, which comprise Δ4, 5 glycuronidase, variant Δ4, 5 glycuronidase of the invention, or therapeutic GAG fragments together with one or more pharmaceutically acceptable carriers and optionally other therapeutic ingredients. The term "pharmaceutically-acceptable carrier" as used herein, and described more fully below, means one or more compatible solid or liquid filler, diluents or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the Δ4, 5 glycuronidase of the present invention or other compositions, and with each other, in a manner such that there is no interaction which would substantially impair the desired pharmaceutical efficiency.

A variety of administration routes are available. The particular mode selected will depend, of course, upon the particular active agent selected, the particular condition being treated and the dosage required for therapeutic efficacy. The methods of this invention, generally speaking, may be practiced using any mode of administration that is medically acceptable, meaning any mode that produces effective levels of the drug without causing clinically unacceptable adverse effects. A preferred mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, transdermal, etc.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, to potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix to of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic to gold particles, contained in liposomes, nebulized, aerosols, pellets for implantation into the skin, or dried onto a sharp object to be scratched into the skin The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The compositions may conveniently be presented in unit dosage form and may be prepared by any of the methods well known in the art of pharmacy. All methods include the step of bringing the active Δ4, 5 glycuronidase into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer may be stored lyophilized.

Other delivery systems can include time-release, delayed release or sustained release delivery systems. Such systems can avoid repeated administrations of the heparinases of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, to some of which are adapted for implantation.

A subject is any human or non-human vertebrate, e.g., dog, cat, horse, cow, pig.

When administered to a patient undergoing cancer treatment, the $\Delta 4, 5$ glycuronidase or therapeutic GAG compounds may be administered in cocktails containing other anti-cancer agents. The compounds may also be administered in cocktails containing agents that treat the side-effects of radiation therapy, such as anti-emetics, radiation protectants, etc.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The $\Delta 4, 5$ glycuronidase or therapeutic GAG compounds may also be linked to a targeting molecule. A targeting molecule is any molecule or compound which is specific for a particular cell or tissue and which can be used to direct the $\Delta 4, 5$ glycuronidase or therapeutic GAG to the cell or tissue. Preferably the targeting molecule is a molecule which specifically interacts with a cancer cell or a tumor. For instance, the targeting molecule may be a protein or other type of molecule that recognizes and specifically interacts with a tumor antigen.

Tumor-antigens include Melan-A/M-ART-1, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, HA, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials And Methods

Chemicals and reagents. Unless otherwise stated, biochemicals were purchased from Sigma Aldrich Chemical (St. Louis, Mo.). Disaccharides were purchased from Calbiochem (San Diego, Calif.). Reagents for λZAP II genomic library construction and screening were obtained from Stratagene (La Jolla, Calif.). Restriction endonucleases were purchased from New England Biolabs (Beverly, Mass.). DNA oligonucleotide primers were manufactured by Invitrogen/Life Technologies (Carlsbad, Calif.). Additional molecular cloning reagents were obtained from the manufacturers listed.

Bacterial strains and growth conditions. *F. heparinum* (*Pedobacter heparinus*) was obtained as a lyophilized stock from American Type Culture Collection (ATCC, Manassas, Va.), stock no. 13125. Rehydrated cultures were grown aerobically at 30° C. with moderate shaking to an optical density ($A_{600}$) between 1.5 and 2 in defined media containing 6.4 mM $NaH_2PO_4$, 7.6 mM $Na_2HPO_4$, 12 mM $KH_2PO_4$, 14.3 mM $K_2HPO_4$, 1.7 mM NaCl, and 1.9 mM $NH_4Cl$, pH 6.9 and supplemented with 0.1 mM trace metals $CaCl_2$, $FeSO_4$, $CuSO_4$, $NaMoO_4$, $CoCl_2$, and $MnSO_4$ (added from a 100× stock in 10 mM $H_2SO_4$), 0.8% glucose, 0.05% methionine, 0.05% histidine, 2 mM $MgSO_4$, and 0.1% heparin all added under sterile conditions. *E. coli* strains included TOP10 (Invitrogen) or DH5a for PCR cloning and subcloning and BL21 (DE3) (Novagen, Madison Wis.) for recombinant protein expression. Bacteriophage host strains XL1-Blue MRF' and SOLR were obtained from Stratagene.

Purification of glycuronidase peptides and protein sequencing. The 4, 5 glycuronidase was purified from 10 liter fermentation cultures using a method such as those described in McLean, M. W., Bruce, J. S., Long, W. F., and Williamson, F. B., 1984, *Eur J Biochem* 145, 607-15.

Molecular Cloning of the Δ4, 5 Glycuronidase Gene from *F. heparinum* Genomic DNA.

Flavobacterial genomic DNA was isolated from 10 mL of Flavobacterial culture using the QIAGEN DNeasy DNA purification kit according to the Manufacturer's instructions for gram-negative bacteria using approximately 2×10⁹ cells per column. Following purification, genomic DNA was ethanol precipitated and resuspended in TE, pH 7.5 at 0.5 mg/mL. The quality of genomic DNA was confirmed spectrophotometrically at 260/280 nm, by electrophoresis on a 0.5% agarose gel and by PCR using Flavobacterial specific primers.

The following degenerate primers were synthesized from peptides corresponding initially to peaks 19 and 24 (Example 1): 5' GARACNCAYCARGGNYTNACNAAYGAR 3' (SEQ ID NO. 5) (peak 19 forward), 5' YTCRTTNGTNARNCCYT-GRTGNGTYTC 3' (SEQ ID NO. 6) (peak 19 reverse); 5' AAYTAYGCNGAYTAYTAYTAY 3' (SEQ ID NO. 7) (peak 24 forward); 5' RTARTARTARTCNGCRTARTT 3' (SEQ ID NO. 8) (peak 24 reverse). All four primers were screened in a PCR assay using all possible pairings (forward and reverse). The PCR reaction conditions included 200 ng of genomic DNA, 200 picomoles for each forward and reverse primer, 200 μM dNTPs, 1 unit of Vent DNA Polymerase (New England Biolabs) in a 100 μl reaction volume. 35 cycles were completed using a 52° C. annealing temperature and 1.5 minute extensions at 72° C. The 450 bp product amplified using primers 19 forward and 24 reverse was gel purified and subject to direct DNA sequencing which confirmed the inclusion of translated sequence corresponding to peptide peaks 19 and 24 in addition to peak 12. The same DNA was also $^{32}P$ radiolabeled by random priming using 200 μCi α$^{32}$P[dCTP] at 6000 Ci/mmole (NEN, Boston, Mass.), 50-100 ng of DNA and the Prime-it II random priming kit (Stratagene) (probe1). Unincorporated $^{32}P$ dNTPs were removed by gel filtration using G-50 Quick-spin columns (Roche Biochemicals, N.J.). Labeling reactions typically yielded approximately 50 ng of radiolabeled DNA with specific activities exceeding $10^9$ cpm/μg.

DNA hybridization probe 2 was initially created by PCR as described above except using degenerate primer 26 5' CAR-ACNTAYACNCCNGGNATGAAY 3' (SEQ ID NO. 9) (peak 26 forward) and 20 picomoles of reverse, non-degenerate primer 54 (5' TTCATGGTCGTAACCGCATG 3') (SEQ ID NO. 10); the latter oligonucleotide corresponds to Δ4, 5 DNA sequence 3' of peak 8. Direct sequencing of this PCR fragment confirmed the presence of peak 26 and peak 13 peptides. DNA probe 3 used in DNA southern hybridizations (below) was PCR amplified from genomic DNA using primer 68 (5' TATACACCAGGCATGAACCC 3') (SEQ ID NO. 11) and 74 (5' CCCAGTATAAATACTCCAGGT 3') (SEQ ID NO. 12).

Plaque hybridization screening of *F. heparinum* genomic library. A X, ZAP II genomic library (Stratagene) was constructed as described [Sasisekharan, R., Bulmer, M., Moremen, K. W., Cooney, C. L., and Langer, R. (1993) *Proc Natl Acad Sci USA* 90, 3660-4]. The amplified library (1×10¹⁰ pfu/mL) was plated out at approximately 1×10⁶ pfu (50,000 pfu/plate) on 100×150 mm LB plates. Plaque lifts on to nylon membranes (Nytran Supercharge, Schleicher and Schuell) and subsequent hybridization screenings were completed using standard methods and solutions [*Current Protocols in Molecular Biology*, 1987, John Wiley and Sons, New York]. DNA was crosslinked to each filter by UV-irradiation (Stratagene Stratalinker) for 30 seconds at 1200 joules/cm³. Hybridizations were carried at 42° C. using 10⁷-10⁸ cpm of radiolabeled probe (at approximately 0.25 ng/mL). Low stringency washes were carried out at room temperature in 2×SSC, 0.1% SDS; high stringency washes carried out at 58-60° C. in 0.2×SSC and 0.1% SDS. Hybridized plaques were visualized by phosphor imaging (Molecular Dynamics) and/or $^{32}P$ autoradiography. Tertiary screens of positive clones were completed and the recombinant phage was excised as a double-stranded phagemid (pBluescript) using the ExAssist interference-resistant helper phage and SOLR strain according to the manufacturer's protocol (Stratagene). Recombinants were characterized by DNA sequencing using both T7 and T3 primers.

Creation of a flavobacterium Bgl II-EcoR1 subgenomic library for isolation of the Δ4, 5 5' terminus. 1 μg of genomic DNA was cut with 20 units of Eco R1, Bgl II, and Hind III individually or as double digests. Restriction products were resolved by gel electrophoresis on 1% agarose gels run in 1×TAE buffer. Southern DNA hybridizations were completed according to standard protocols [*Current Protocols in Molecular Biology*, 1987, John Wiley and Sons, New York] using $^{32}P$ radiolabeled probe 3. Based on this Southern analysis, 5 μg of Flavobacterial genomic DNA was digested with Bgl-II-Eco R1 and the DNA resolved on a preparative 1% agarose gel run under identical conditions as those described for the analytical gel. DNA ranging from approximately 1-2 kb was gel purified and ligated into pLITMUS as a Bgl II-EcoR1 cassette. Positive clones were identified by PCR colony screening using primers 68 and 74 and confirmed by DNA sequencing.

PCR cloning of Δ4, 5 gene and recombinant expression in *E. coli*. The full-length glycuronidase gene was directly PCR amplified from genomic DNA using forward primer 85 5' TGTTCTAGACATATGAAATCACTACTCAGTGC (SEQ ID NO. 13) 3' and reverse primer 86 5' GTCTCGAGGATC-CTTAAGACTGATTAATTGTT 3' (SEQ ID NO. 14) (with Nde 1 and Xho1 restriction sites denoted in bold), 200 ng genomic DNA, and Vent DNA Polymerase for 35 cycles. dA overhangs were generated in a final 10 minute extension at 72° C. using AmpliTaq DNA polymerase (Applied Biosystems). PCR products were gel purified, ligated into the TOPO/TA PCR cloning vector (Invitrogen), and transformed into One-shot TOP10 chemically competent cells. Positive clones were identified by blue/white colony selection and confirmed by PCR colony screening. The 1.2 kb Δ4, 5 gene was subcloned into expression plasmid pET28a (Novagen) as an Nde 1-Xho 1 cassette. Final expression clones were confirmed by plasmid DNA sequencing.

For the expression of Δ4, 5 glycuronidase beginning with M21 (Δ4,5$^{Δ20}$), the forward primer 95 5' TGT TCT AGA CAT ATG ACA GTT ACG AAA GGC AA 3' (SEQ ID NO. 15) (also containing an Nde 1 restriction site near its 5' terminus) was used in place of primer 85 (above). 50 ng of the original expression plasmid pET28a/Δ4, 5 was used as the DNA template in PCR reactions involving a total of 20 cycles. Otherwise, cloning was as described for the full-length gene. Both pET28a/Δ4, 5 and pET28aΔ4,5$^{Δ20}$ plasmids were transformed into BL21 (DE3) for expression as N-terminal 6× His tagged proteins. 1 liter cultures were grown at room temperature (~20° C.) in LB media supplemented with 40 µg/mL kanamycin. Protein expression was induced with 500 µM IPTG added at an $A_{600}$ of to 1.0. Induced cultures were allowed to grow for 15 hours (also at room temperature).

Recombinant Δ4, 5 glycuronidase purification. Bacterial cells were harvested by centrifugation at 6000×g for 20 minutes and resuspended in 40 mL of binding buffer (50 mM Tris-HCL, pH 7.9, 0.5 M NaCl, and 10 mM imidazole). Lysis was initiated by the addition of 0.1 mg/mL lysozyme (20 minutes at room temperature) followed by intermittent sonication in an ice-water bath using a Misonex XL sonicator at 40-50% output. The crude lysate was fractionated by low-speed centrifugation (18,000×g; 4° C.; 15 minutes) and the supernatant was filtered through a 0.45 micron filter. The 6×-His tag Δ4, 5 glycuronidase was purified by Ni$^{+2}$ chelation chromatography on a 5 mL Hi-Trap column (Pharmacia Biotech, New Jersey) pre-charged with 200 mM NiSO$_4$ and subsequently equilibrated with binding buffer. The column was run at a flow rate of approximately 3-4 mL/minute that included an intermediate wash step with 50 mM imidazole. The Δ4, 5 enzyme was eluted from the column in 5 mL fractions using high imidazole elution buffer (50 mM Tris-HCL, pH 7.9, 0.5 M NaCl, and 250 mM imidazole). Peak fractions were dialyzed overnight against 4 liters of phosphate buffer (0.1M sodium phosphate, pH 7.0, 0.5 M NaCl) to remove the imidazole.

The 6× His tag was effectively cleaved by adding biotinylated thrombin at 2 units/milligram of recombinant protein, overnight at 4° C. with gentle inversion. Thrombin was captured by binding to streptavidin agarose at 4° C. for two hours using the Thrombin Capture Kit (Novagen). The cleaved peptide 5' MGSSHHHHHHSSGLVPR 3' (SEQ ID NO. 16) was removed by final dialysis against a 1000-fold volume of phosphate buffer.

Protein concentrations were determined by protein assay (Bio-Rad, Hercules, Calif.) and confirmed by UV spectroscopy using a theoretical molar extinction coefficient ε=88,900 for Δ4,5$^{Δ20}$. Protein purity was assessed by SDS-PAGE followed by Coomassie Brilliant Blue staining.

Computational methods. Signal sequence predictions were made by SignalP V1.1 using the von Heijne computational method [Nielsen, H., Engelbrecht, J., Brunak, S., and von Heijne, G., 1997, *Protein Eng* 10, 1-6] with maximum Y and S cutoffs set at 0.36 and 0.88, respectively. Glycuronidase multiple sequence alignments were made from select BLASTP database sequences (with scores exceeding 120 bits and less than 6% gaps) using the CLUSTAL W program (version 1.81) preset to an open gap penalty of 10.0, a gap extension penalty of 0.20, and both hydrophilic and residue-specific gap penalties turned on.

Assay for enzyme activity and determination of kinetic parameters. Standard reactions were carried out at 30° C. and included 100 mM sodium phosphate buffer, pH 6.4, 50 mM NaCl, 500 µM disaccharide substrate and 200 nM enzyme in a 100 µl reaction volume. Hydrolysis of heparin disaccharides was determined spectrophotometrically by measuring the loss of the Δ4, 5 chromophore measured at 232 nm Substrate hydrolysis was calculated using the following molar extinction coefficients empirically determined for each disaccharide substrate: $\Delta UH_{NAc}$, $\epsilon_{232}$=4,524; $\Delta UH_{NAc6S}$, $\epsilon_{232}$=4,300; $\Delta UH_{NS}$, $\epsilon_{232}$=6,600; $\Delta UH_{NS,6S}$, $\epsilon_{232}$=6,075; $\Delta UH_{NH26S}$, $\epsilon_{232}$=4,826; $\Delta U_{2S}H_{NS}$, $\epsilon_{232}$=4,433. Initial rates ($V_o$) were extrapolated from linear activities representing <10% substrate turnover and fit to pseudo first-order kinetics. For kinetic experiments, disaccharide concentration for each respective substrate was varied from 48 to 400 µM concentrations. $K_m$ and $k_{cat}$ values were extrapolated from $V_o$ vs. [S] curves fit to the Michaelis Menten equation by a non-linear, least squares regression.

For experiments measuring the relative effect of ionic strength on glycuronidase activity, the NaCl concentration was varied from 0.05 to 1 M in 0.1 M sodium phosphate buffer (pH 6.4), 200 µM $\Delta UH_{NS,6S}$ and 100 µM enzyme under otherwise standard reaction conditions. The effect of pH on catalytic activity was kinetically determined at varying $AUH_{NS,6S}$ concentrations in 0.1 M sodium phosphate buffer at pH 5.2, 5.6, 6.0, 6.4, 6.8, 7.2 and 7.8. Data were fit to Michaelis-Menten kinetics as described above and the relative $k_{cat}/K_m$ ratios plotted as a function of pH.

Detection of Δ4, 5 glycuronidase activity by capillary electrophoresis. 200 µg of heparin (Celsus Laboratories) was subject to exhaustive heparinase digestion as described [Venkataraman, G., Shriver, Z., Raman, R., and Sasisekharan, R., 1999, *Science* 286, 537-42] with certain modifications that included a 50 mM PIPES buffer, pH 6.5 with 100 mM NaCl in a 100 µl reaction volume. Following heparinase treatment, 25 picomoles of Δ4, 5 glycuronidase was added to one-half of the original reaction (pre-equilibrated at 30° C.). 20 µl aliquots were removed at 1 minute and 30 minutes and activity quenched by heating at 95° C. for 10 minutes. 20 µl of the minus Δ4, 5 control (also heated for 10 minutes) was used as the 0 time point. Disaccharide products were resolved by capillary electrophoresis run for 25 minutes under positive polarity mode as previously described [Rhomberg, A. J., Ernst, S., Sasisekharan, R., and Biemann, K., 1998, *Proc Natl Acad Sci USA* 95, 4176-81].

Molecular mass determinations. Molecular mass determinations were carried out by MALDI-MS as described

[Rhomberg, A. J., Ernst, S., Sasisekharan, R., and Biemann, K., 1998, *Proc Natl Acad Sci USA* 95, 4176-81].

Example 1

Molecular Cloning of Δ4, 5 Glycuronidase Gene from *F. heparinum* Genome

To clone the Δ4, 5 glycuronidase gene, we isolated a series of Δ4, 5 glycuronidase-derived peptides after protease treatment of the purified enzyme. The native enzyme was directly purified from fermentation cultures of *F. heparinum* using a 5-step chromatography scheme as previously described [McLean, M. W., Bruce, J. S., Long, W. F., and Williamson, F. B., 1984, *Eur J Biochem* 145, 607-15]. The extent of purity was ultimately characterized by reverse phase chromatography, which indicated a single major peak (FIG. 1A). We were able to generate a number of peptides by a limited trypsin digestion of the purified enzyme. 26 peptide fragments were resolved by reverse phase chromatography (FIG. 1B). From these 26, at least eight peptides (corresponding to major peaks 8, 12, 13, 19, 24, and 26) were of sufficient yield and purity and were selected for protein sequence determination (FIG. 1C).

Based on this information, we designed degenerate primers corresponding to peaks 19, 24, and 26. These primers were used to PCR amplify Δ4, 5 specific sequences to be used as a suitable DNA hybridization probes for screening the Flavobacterial genomic library. A combination of two primer pairs in particular (peak 19 forward and peak 24 reverse) gave a discrete PCR product of approximately 450 base pairs. The translation of the corresponding DNA sequence indicated that it contained the expected amino acid sequence corresponding to peaks 19 and 24. The peak 12 peptide also mapped to this region. We used this discrete PCR amplified DNA fragment (designated as probe 1, FIG. 2A) in the initial plaque hybridizations. The most 5' terminal clone obtained in this screening (represented by clone GSA) included approximately one-half of the predicted gene size corresponding to the carboxy terminus of the putative ORF. Invariably, all of the isolated clones possessed and Eco R1 site at their respective 5' termini In an attempt to isolate a clone from the phage library possessing the other half of the gene, we rescreened additional plaques, this time using a second N-terminal specific DNA hybridization probe (probe 2) in tandem with the original probe 1. This second strategy also failed to yield any clones with the fully-intact Δ4, 5 gene. A partial, overlapping clone (G5H), however, did extend the known 5' sequence of Δ4, 5 by approximately 540 base pairs.

Figure 2B:
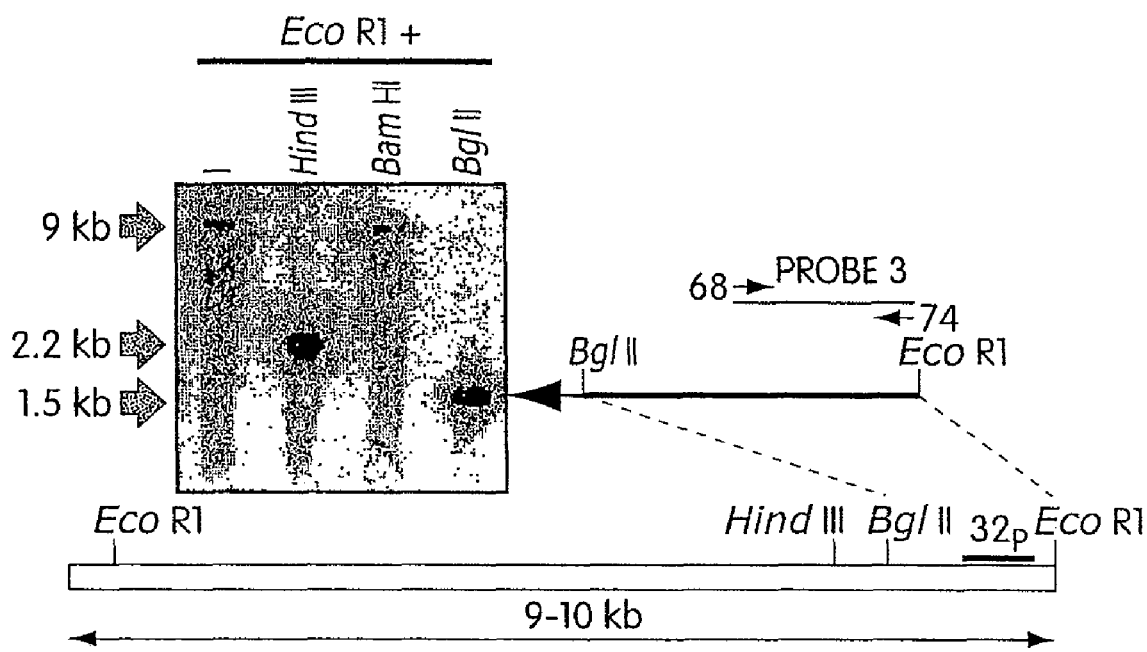

Alternate approaches were taken in an attempt to obtain the 5' terminus of the glycuronidase gene. The size of this missing region was estimated, based on the molecular weight of the native protein, to be approximately 45 amino acids (or 135 base pairs). We completed DNA southern analyses to identify potentially useful DNA restriction sites flanking the 5' end of the Δ4, 5 gene (FIG. 2B). This restriction mapping ultimately involved the use of the Eco R1 site within the gene in conjunction with hybridization probe 3 (whose 3' end lies just 5' to this restriction site) to positively bias our search for the remaining amino terminus Based on this refined map, we successfully isolated and subcloned an approximately 1.5 kb Bgl II-Eco R1 Δ4, 5 fragment into pLITMUS. The 5' terminus of the Δ4, 5 gene was obtained from direct DNA sequencing of this subgenomic clone.

Results

Figure 2C:
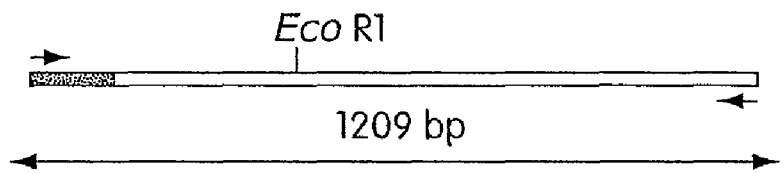
Figure 4A:
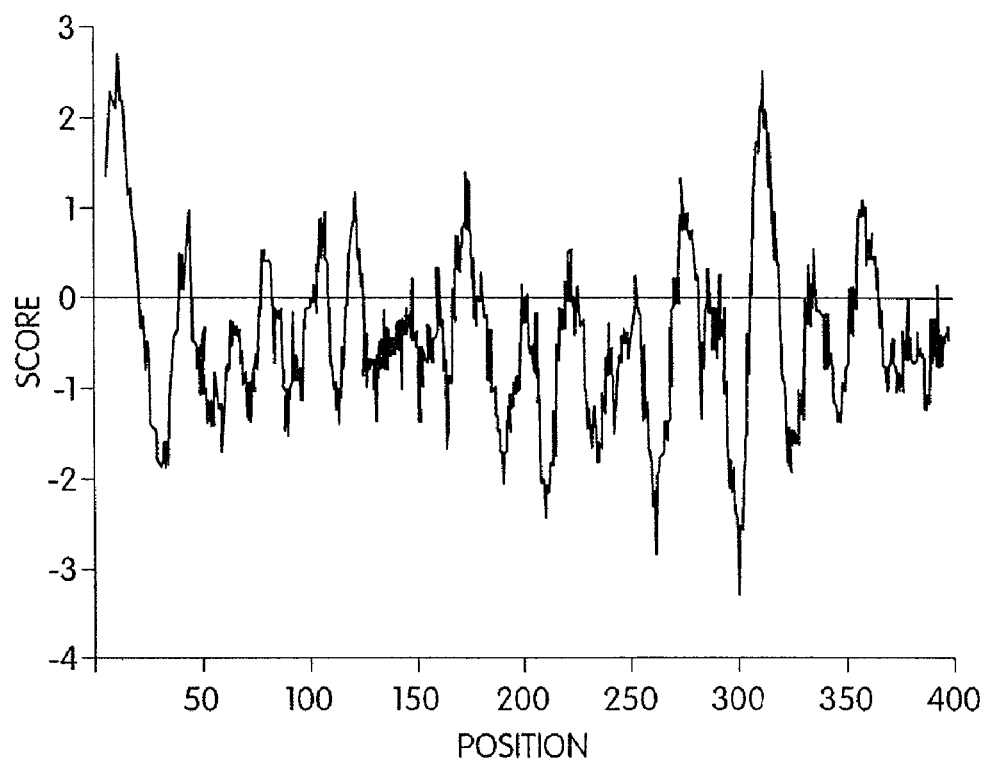
FIG. 4 illustrates the Δ4, 5 glycuronidase primary sequence analyses. A. Hydropathy plot (Kyte-Doolittle). Positive values represent increasing hydrophobicity. B. Theoretical signal sequence determination using amino acids 1-65. Indices were calculated using SignalP V.1.1 using networks trained on gram-negative bacteria. Putative cleavage site located between G20 and M21 is represented by a vertical arrow. C. CLUSTAL W multiple alignment of full-length Δ4, 5 glycuronidase with select glucuronyl hydrolases. Protein sequences were selected from an initial BLASTP search of the protein database. to Identical amino acids are shaded in dark gray, near invariant positions in charcoal, and conservative substitutions in light gray. Gen Bank accession numbers are as follows: *Bacillus* sp. (AB019619); *Streptococcus pneumoniae* (AE008410); *Streptococcus pyogenes* (AE006517); *Agaricus bisporus* (AJ271692); *Bactobacillus halodurans* (AP001514).
Figure 4B:
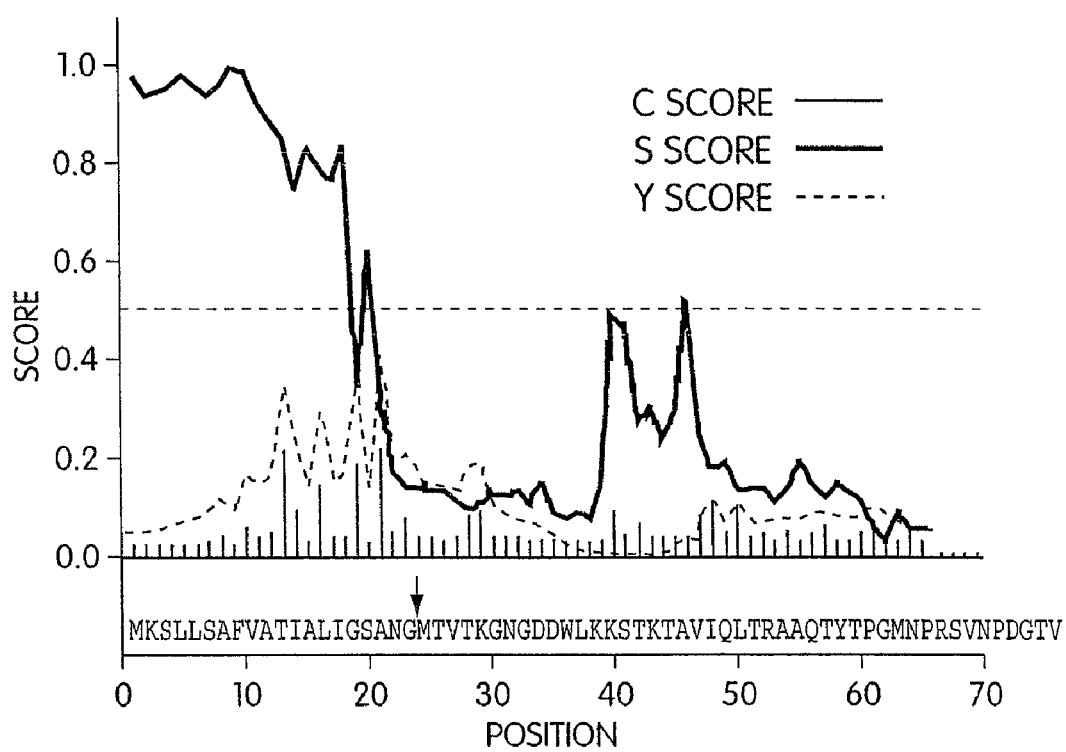

A summary of the full-length gene obtained from the two overlapping cloning methods is depicted in FIG. 2C. The DNA sequence analysis compiled from the overlapping Δ4, 5 clones (and confirmed by direct sequencing of a single PCR amplified genomic clone) is shown in FIG. 3. The Δ4, 5 coding sequence is comprised of 1209 base pairs corresponding to an ORF that encodes a 402 amino acid protein. The amino acid and nucleotide sequences for the full-length enzyme are given as SEQ ID Nos.:3 and 4, respectively. The predicted molecular weight of 45,621 daltons for the translated protein corresponds very well with an empirical molecular mass of 45,566 daltons for the purified Flavobacterial enzyme determined by MALDI-MS. All of the peptides for which we obtained sequence information map to this Δ4, 5 ORF. Based on further primary sequence analyses, we have also identified a likely bacterial signal sequence spanning amino acids 1-20 also possessing a putative cleavage site between residues G20 and M21 (FIG. 4B). The presence of a markedly hydrophobic amino terminus (see hydropathy plot, FIG. 4A) and the identification of an AXXA peptidase cleavage motif further support this assumption [von Heijne, G., 1988, *Biochim Biophys Acta* 947, 307-33].

A search for related sequences in the NCBI protein database led to several functionally related enzymes. In a multiple sequence alignment of our cloned enzyme with select glucuronyl hydrolases, we found a homology that generally corresponded to upwards of 30% identity and nearly 50% similarity at the primary sequence level (FIG. 4C). This relatedness spanned most of the enzyme sequence, excluding the N-terminus Based on this alignment, we found several highly conserved positions within the *F. heparinum* Δ4, 5 glycuronidase that included, in particular, several aromatic and acidic residues. Other invariant amino acids of possible catalytic importance include H115 and R151.

Example 2

Recombinant Expression and Purification of the Δ4, 5 Glycuronidase

Using PCR, we cloned from the *F. heparinum* genome both the full-length enzyme and the "mature" enzyme lacking the N-terminal 20 amino acid signal sequence ($\Delta 4,5^{\Delta 20}$) into a T7-based expression plasmid. Cloning into pET28a permitted the expression of the glycuronidase as an N-terminal 6× His-tag fusion protein. Pilot expression studies focused on the full-length enzyme. In these initial experiments, we examined several different induction conditions such as temperature, time and length of induction, and even IPTG concentrations. In every case, the full-length enzyme was present nearly exclusively as an insoluble fraction. Attempts to purify the enzyme directly from inclusion bodies and then refold the apparently mis-folded protein were initially not successful; while solubility was partially achieved by a combined use of detergents (e.g., CHAPS), increasing salt concentrations, and the presence of glycerol, the partially purified enzyme was largely inactive.

A possible explanation for this insolubility points to the presence of a very hydrophobic region within the wild-type protein sequence spanning the first 20 amino acids. The N-terminal sequence is also predicted to comprise a cleavable prokaryotic signal sequence with the most likely cleavage site occurring between position G20 and M21 (FIG. 3). Within this sequence, we also find the alanine repeat 5' AXXAXX-AXXXXA 3' (SEQ ID NO. 17) that may serve as part of the actual cleavage recognition sequence [von Heijne, G., 1988, *Biochim Biophys Acta* 947, 307-33]. This signal peptide would indicate a periplasmic location for the glycuronidase with the N-terminus of the secreted (mature) protein beginning with M21. We recombinantly expressed this mature variant ($\Delta 4,5^{\Delta 20}$) in which the signal sequence was replaced entirely by an N-terminal 6× His purification tag. Recombinant expression of the enzyme lacking the presumed signal sequence yielded remarkably different results. In this case, soluble recombinant expression levels routinely reached several hundred milligrams of protein per liter of induced cells. The specific activity of this enzyme on the heparin disaccharide $\Delta UH_{Nac}$ was likewise robust.

Results

Figure 5:
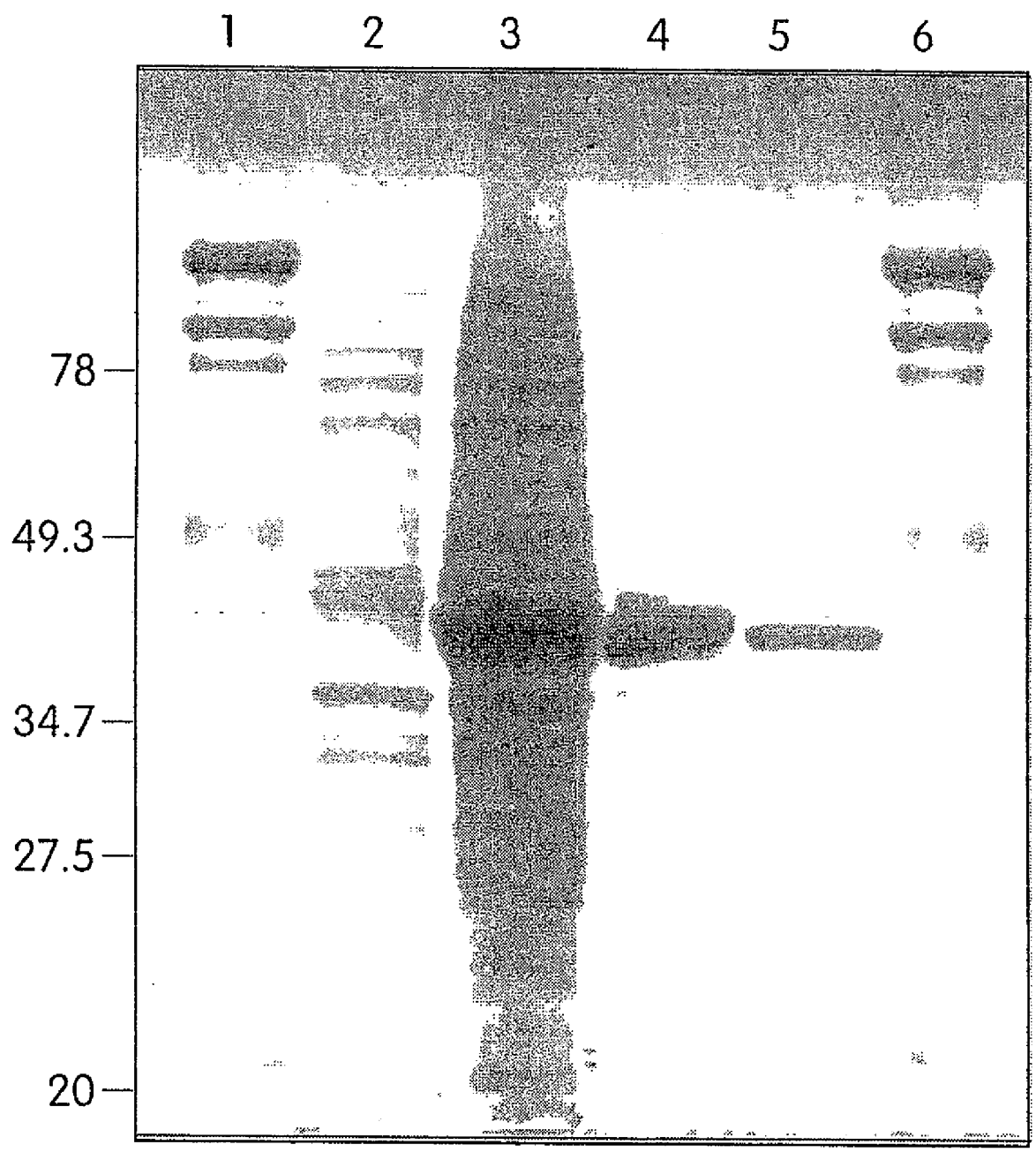
FIG. 5 provides results of recombinant $Δ4,5^{Δ20}$ protein expression and purification. The amino acid and nucleic acid sequences are given as SEQ ID NOS: 1 and 2, respectively. SDS-PAGE of Δ4, 5 protein fractions at various purification stages following expression in BL21 (DE3) as a 6×HIS N-terminal fusion protein. Shown here is a 12% gel that is stained with Coomassie-Brilliant blue. Lane 2, lysate from uninduced bacterial cells; Lane 3, crude cell lys ate from induced cultures; Lane 4, $Ni^{+2}$ chelation chromatography purification; Lane 5, thrombin cleavage to remove N-terminal 6× His purification tag. Molecular weight markers (Lanes 1 and 6) are also noted.

A summary of the expression and purification of $\Delta 4,5^{\Delta 20}$ is summarized in FIG. 5 and Table 1. A two-step purification comprised of $Ni^{+2}$ chelation chromatography followed by thrombin cleavage to remove the 6× His purification tag, typically yielded over 200 mg of greater than 90% pure enzyme as assessed by SDS-PAGE followed by Coomassie Brilliant Blue staining. An approximately three-fold purification of activity was achieved in a single chromatographic step. Most notably, the specific activity of the recombinant enzyme acting upon $\Delta UH_{NAc}$ far exceeded those values reported in the literature [Warnick, C. T. and Linker, A., 1972, *Biochemistry* 11, 568-72]. While removal of the 6× His tag from the N-terminus of the enzyme was unnecessary for optimal hydrolytic activity, the presence of the histidine tag did appear to instigate protein precipitation over an extended time especially at higher enzyme concentrations. This tag was, therefore removed for all subsequent biochemical experiments. In this manner, the recombinant protein was stable at 4° C. for at least two weeks during which time it remained in solution at protein concentrations exceeding 10 mg/mL under the buffer conditions described.

A molecular mass of 44,209 daltons was determined for the recombinant enzyme (i.e., $\Delta 4,5^{\Delta 20}$) by MALDI-MS. The amino acid and nucleotide sequence for the enzyme which lacks the N-terminal 20 amino acid signal sequence is given as SEQ ID Nos.:1 and 2, respectively. This empirically-established molecular weight is consistent with its theoretical value of 43,956 Daltons based on its amino acid composition. This value physically differs by 1357 Daltons in comparison to a molecular weight of 45,566 daltons likewise measured for the native enzyme. This mass differential is largely accounted for by the engineered removal in the recombinant protein of the 20 amino acid signal sequence. However, we cannot exclude the possibility of differential posttranslational modifications such as glycosylation largely accounting for the observed differences between the two enzyme populations. Unfortunately, chemical blocking precluded us from determining the N-terminal sequence of the native protein.

TABLE 1

Purification summary for the recombinant $\Delta 4$, 5 glycuronidase. Specific activities for each fraction were measured using 800 ng of protein and 120 μM of the unsulfated heparin disaccharide (DiS) $\Delta UH_{NAc}$ in a 100 μl reaction volume. The fold purification was calculated relative to the specific activity measured for the crude lysate.

| Purification Step | Protein Yield (mg) | Sp. Activity (μmoles DiS/min./mg protein) | % purification |
|---|---|---|---|
| Crude lysate | 400 | 4.7 | — |
| $Ni^{+2}$ chromatography | 205 | 12.9 | 2.7 |
| Thrombin cleavage | 205 | 13.6 | 2.9 |

Example 3

Biochemical Conditions for Optimal Enzyme Activity

Figure 6A:
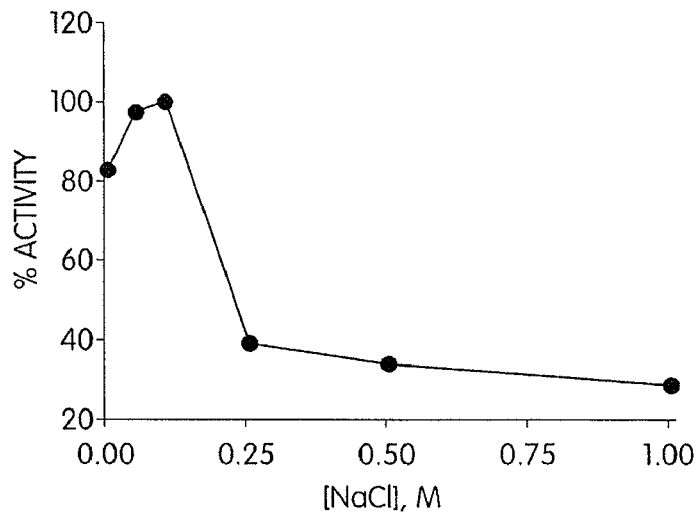
FIG. 6 depicts the effects of Δ4, 5 glycuronidase biochemical reaction conditions. A. [NaCl] titration; B. Effect of reaction temperature C. pH profile. Relative enzyme activities were derived from the initial rates normalized to 100 mM NaCl (A) or 30° C. (C). $k_{cat}$ and $K_m$ values for the pH profile were extrapolated from Michaelis-Menten kinetics as described in the Methods (and FIG. 8) The disulfated heparin disaccharide $ΔUH_{NS,6S}$ was used in all three experiments.

To determine the optimal reaction conditions for $\Delta 4$, 5 glycuronidase activity, we analyzed initial reaction rates as a function of buffer, pH, temperature, and ionic strength (FIG. 6). For these experiments, we used the disulfated heparin disaccharide substrate $\Delta UH_{NS,6S}$. Based on what is known about the degradation of heparin/heparan sulfate-like glycosaminoglycans by flavobacteria as well as initial biochemical characterization of this and related enzymes [Warnick, C. T. and Linker, A., 1972, *Biochemistry* 11, 568-72], we hypothesized that a heparin disaccharide would be an optimal substrate for the $\Delta 4$, 5 glycuronidase. Enzyme activity was routinely monitored by a loss of absorbance at 232 nm, corresponding indirectly to the hydrolysis of the uronic acid from the non-reducing end.

Results

Under these conditions, we observed a NaCl concentration-activity dependence that was optimal between 50 and 100 mM. NaCl concentrations exceeding 100 mM demonstrated a significant and relatively sharply negative effect on specific activity (FIG. 6A), i.e., with approximately 60% inhibition occurring at 250 mM NaCl relative to 100% activity measured at 100 mM NaCl. The steep transition observed in the NaCl titration curve suggests an important role of ionic interactions in some aspect of enzymatic function.

Figure 6B:
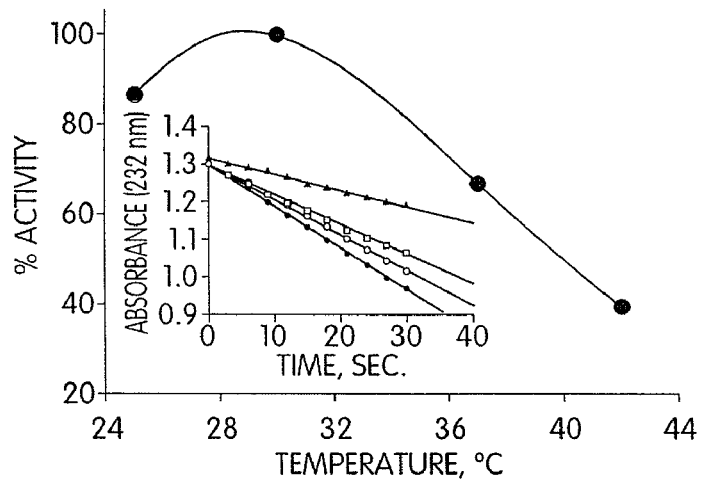
Figure 6C:
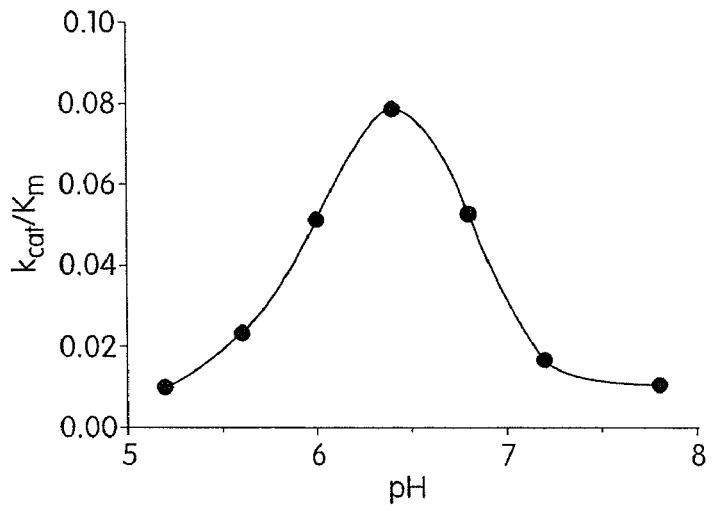

The observed pH profile for the glycuronidase is bell-shaped (FIG. 6C) with a pH optimum of 6.4. Interestingly, initial reaction rates are significantly reduced at the highest temperatures measured, especially at 42° C. (FIG. 6B). Preincubation experiments at 30, 37, and 42° C. to assess relative enzyme stabilities at these temperatures, however, indicated no significant change in relative enzyme activities when subsequently measured under the standard 30° C. reaction conditions. The results of such an experiment strongly suggest that thermal lability is not the issue.

As a final variable for optimizing $\Delta 4$, 5 glycuronidase in vitro reaction conditions, we also considered any requirement for divalent metal ions. We found no evidence that metals are either required for catalysis or activate the enzyme to any appreciable extent.

Figure 7:
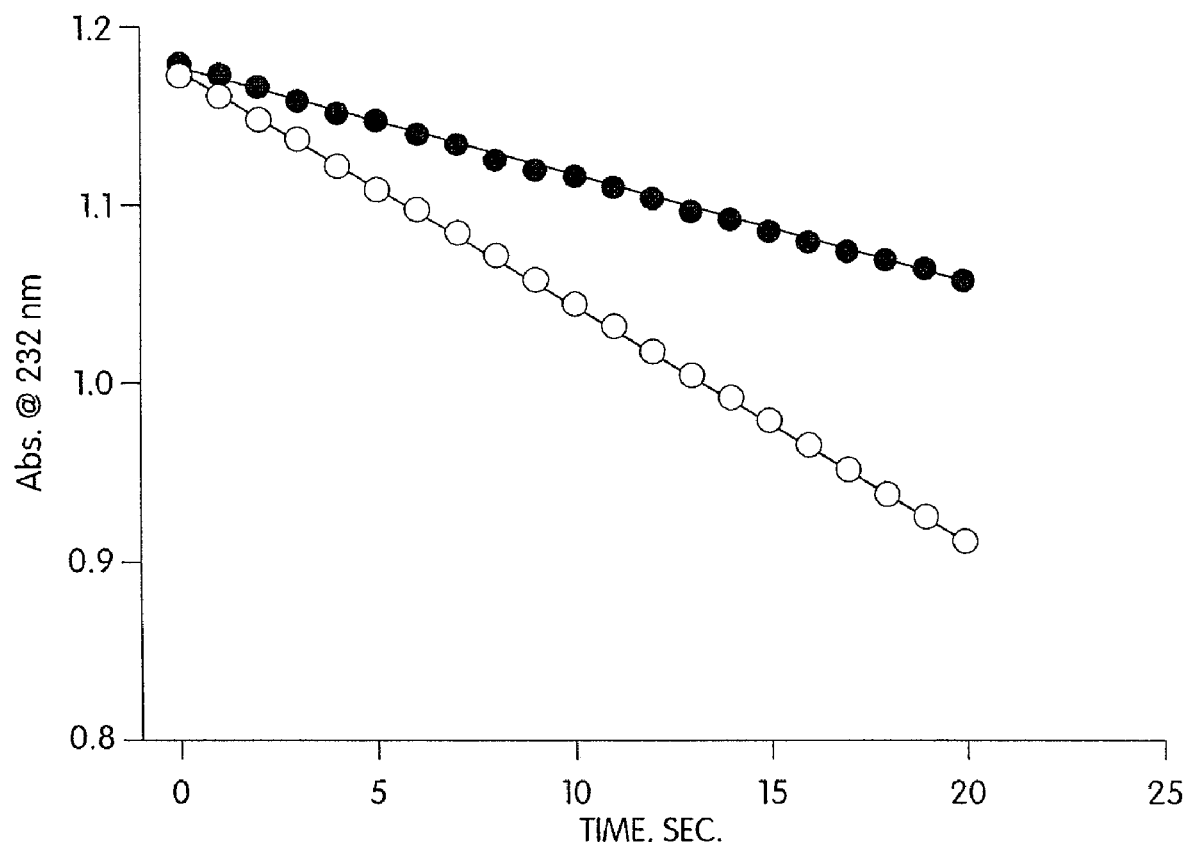
FIG. 7 depicts a kinetic comparison of native and recombinant enzymes. Relative specific activities were measured for both enzyme fractions under identical reaction conditions that included 200 nM enzyme and 500 μM of the heparin disaccharide substrate (ΔUHNAc). Flavobacterial Δ4, 5 (closed circles); recombinant Δ4, 5 (open circles).

Having established the reaction conditions for optimal $\Delta 4$, 5 glycuronidase activity, we next compared the specific activity of the recombinant enzyme ($\Delta 4,5^{\Delta 20}$) relative to the native enzyme purified directly from *F. heparinum* (FIG. 7). The activities of both enzyme fractions were measured in parallel under identical reaction conditions. In this comparison, the recombinant $\Delta 4$, 5 possessed an approximately three-fold higher specific glycuronidase activity relative to the native enzyme. These observed rates demonstrate quite clearly that the cloned $\Delta 4$, 5 enzyme possesses "wild-type" activity that is in no way adversely affected by its recombinant expression in *E. coli*.

Example 4

$\Delta 4$, 5 Glycuronidase Substrate Specificity

Figure 8A:
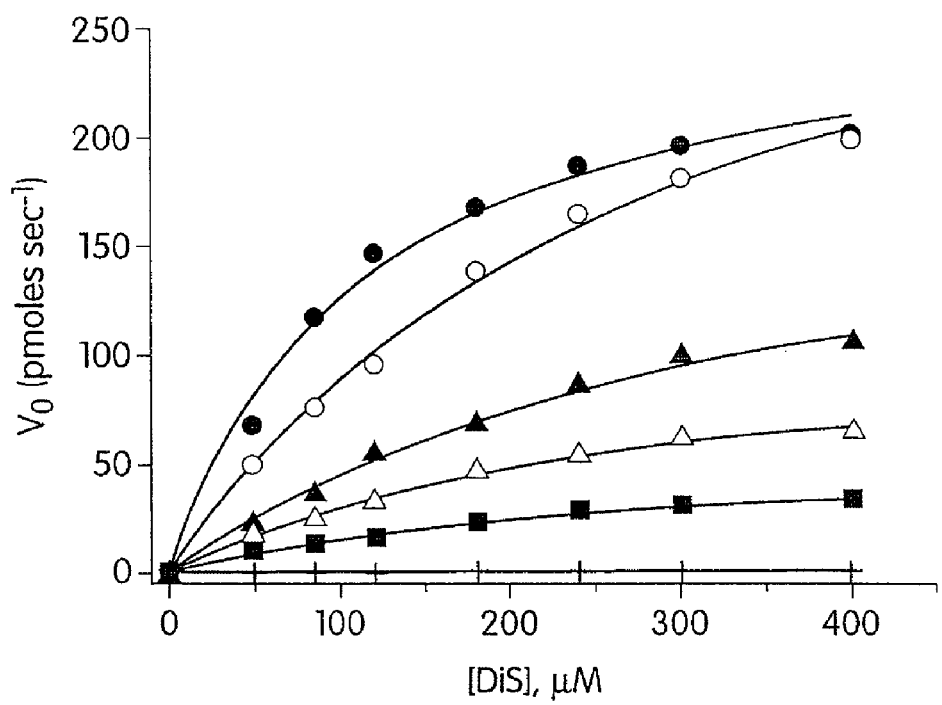
FIG. 8 illustrates disaccharide substrate specificity. A. Kinetic profiles for heparin disaccharides of varying sulfation. Initial rates were determined using 200 nM enzyme under standard conditions. Vo vs. [S] curves were fit to Michaelis-Menten steady state kinetics using a non-linear least squares analysis. B. Lineweaver-Burke representation of the data shown in A. $ΔUH_{Nac,S6}$ (●); $ΔUH_{Nac}$ (○); $ΔUH_{NS,6S}$ (▲); $ΔH_{NS}$ (Δ); $ΔUH_{NH2,16S}$ (+) $ΔU_{2S}H_{NS}$ (+, no activity).
Figure 8B:
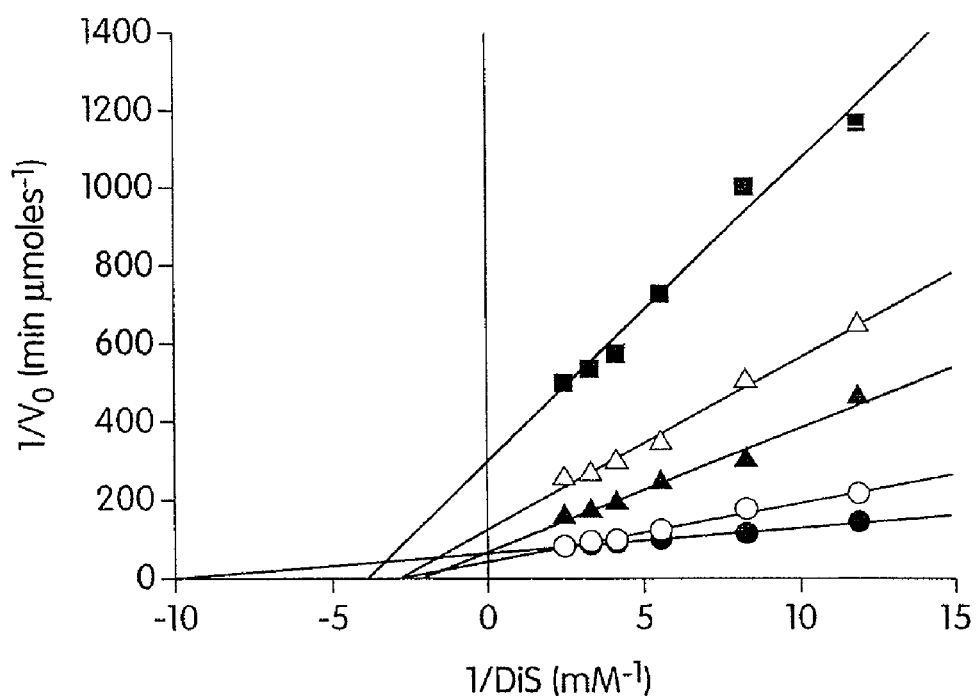

The specificity of the $\Delta 4$, 5 glycuronidase acting on various glycosaminoglycan disaccharide substrates was investigated. The various substrates examined included both heparin and chondroitin disaccharides as well as an hyaluronadate. In particular, we considered the possibility of any structural discriminations pertaining to glycosidic linkage position (1→4 vs. 1→3) and relative sulfation state within the disaccharide. For each substrate, kinetic parameters were determined based on substrate saturation profiles that fit Michaelis-Menten assumptions (FIG. 8). These kinetic values are listed in Table 2. For the heparin disaccharides, $k_{cat}$ values varied significantly from approximately 2 to 15 sec$^{-1}$, while the apparent $K_m$ values for each respective disaccharide were comparable, ranging from approximately 100-300 µM.

Results

The heparin disaccharide $\Delta U_{2S}H_{NS}$ was not a substrate at any of the concentrations studied, even following an extended incubation time spanning several hours. For those heparin disaccharides that were hydrolyzed under the conditions tested and for which kinetic parameters could be determined, an interesting substrate preference was apparent. In this hierarchy and under these conditions, the two disaccharides $\Delta UH_{NAc}$ and $\Delta UH_{Nac6s}$ were the best substrates; in comparison, $\Delta UH_{NH26S}$ and $\Delta UH_{NS}$ were less good as substrates. The kinetic values for $\Delta UH_{NS,6S}$ fell roughly in the middle between these two boundaries.

The data show that heparin is a better substrate than chondroitin/dermatan and/or hyaluronan, although these compounds are also substrates. None of the non-heparin disaccharides were hydrolyzed under the conditions for measuring substrate kinetics. This result indicates an unequivocal discrimination of the Δ4, 5 in regard to linkage position, with a strong preference for 1→4 versus 1→3 linkages. At the same time, these disaccharides were slowly hydrolyzed to varying degrees when the enzyme reactions were conducted over a much longer timecourse (>12 hours) and at considerably higher enzyme concentrations. After approximately 18 hours, greater than 80% of monosulfated chondroitin disaccharide ($\Delta UGal_{Nac6S}$) was hydrolyzed, whereas the non-sulfated chondroitin ($\Delta UGal_{NAc}$) and the hyaluronan disaccharide (ΔUH) were still present at approximately 40% and 65%, respectively. The importance of the linkage position is, therefore, not absolute. The apparently positive effect of chondroitin 6-O-sulfation within the galactosamine is consistent with our results for the heparin substrates and provides further evidence for the influence of this position in dictating substrate specificity.

Based on the kinetically defined substrate specificity for the disaccharides, we set out to validate these results while, at the same time, to investigate the utility of the Δ4, 5 glycuronidase as an enzymatic tool for HSGAG compositional analyses. In this manner, the Δ4, 5 should be very useful in assessing the composition of disaccharides resulting from prior heparinase treatment of heparin/heparan sulfate. For this particular experiment, we pre-treated 200 µg of heparin with a heparinase cocktail. This exhaustive digestion was then directly followed by a relatively short (1 minute) or long (30 minute) Δ4, 5 glycuronidase treatment carried out under optimal reaction conditions. The disaccharide products were then resolved by capillary electrophoresis. The electrophoretic mobility profile for the Δ4, 5 treated saccharides were then directly compared to the untreated control (i.e., heparinase treatment only) run under identical conditions (FIG. 9). 7 disaccharide peaks were present in the capillary electrophoretogram corresponding to the heparinase only control (A.). A structural assignment for each one of these peaks was made based on previously established compositional analyses. For the most part, the resolution of these Δ4, 5 containing saccharides was such that each alternating peak (1, 3, 5, . . . ) corresponded to to a disaccharide possessing a 2-O sulfated uronic acid at the non-reducing end. Predictably, the relative amplitude and area of these peaks remained the same, over the entire timecourse of the Δ4, 5 preincubation. This unchanging result extended to 18 hours. On the other hand, peaks corresponding to disaccharides lacking the 2-O sulfate were eliminated. Moreover, the relative rates of their disappearances elegantly corresponded to their respective preferences as substrates as determined in the previous kinetic experiment. $\Delta UH_{NAc6S}$ (peak 8) was essentially hydrolyzed within one minute; $\Delta UH_{NS,6S}$ (peak 4) a $\Delta UH_{NS}$ (peak 6) were approximately 75% and 50% hydrolyzed, respectively. These two latter substrates were completely depleted by 30 minutes.

Figure 9:
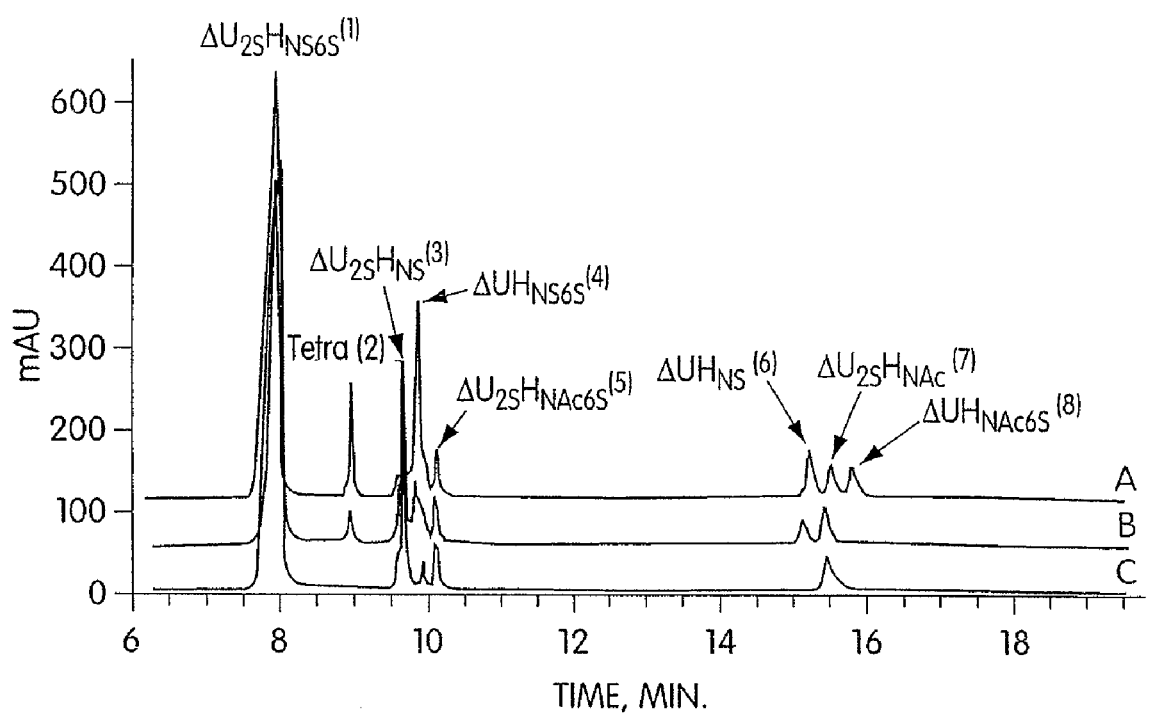
FIG. 9 depicts the tandem use of heparinases and Δ4, 5 glycuronidase in HSGAG compositional analyses. 200 μg heparin was exhaustively digested with heparinases I, II, and III, after which Δ4, 5 was added for a varying length of time. disaccharide products were resolved by capillary electrophoresis. Assignment of saccharide composition shown for each peak was confirmed by MALDI-MS. A., minus Δ4, 5 enzyme control; dashed line, B., minute (partial) Δ4, 5 incubation; C., 30 minute (exhaustive) Δ4, 5 incubation.

In addition to the assigned disaccharides, the Δ4, 5 glycuronidase also acted on a heparinase-generated tetrasaccharide (identified as peak 2 in FIG. 9). The assignment of Peak 2 as a tetrasaccharide was confirmed by MALDI-MS indicating a mass of 1036.9 that corresponds to a singly acetylated tetrasaccharide with four sulfates. Disaccharide analysis of this tetrasaccharide further indicated that it does not contain a 2-O sulfate at the non-reducing end. The Δ4, 5 enzyme hydrolyzed approximately one-half of the starting material after one minute. The relative rate of hydrolysis for this tetrasaccharide roughly corresponded to the rate observed for the disaccharide $4UH_{NS}$ (peak 6). This exciting result clearly indicates that a longer chain saccharide such as a tetrasaccharide is in fact a substrate for the Δ4, 5 catalyzed hydrolysis.

TABLE 2

Kinetic parameters for heparin disaccharides. $k_{cat}$ and $K_m$ values were determined from non-linear regression analyses of the Michaelis-Menten curves presented in FIG. 9.

| Disaccharide substrates | $k_{cat}$ (sec$^{-1}$) | $K_m$ (µM) | $k_{cat}/K_m$ | Relative $k_{cat}/K_m$ |
|---|---|---|---|---|
| $\Delta UH_{Nac}$ | 15.3 ± 0.9 | 283 ± 31 | 0.054 | 0.49 |
| $\Delta UH_{NAc, 6S}$ | 11.7 ± 0.6 | 107 ± 15 | 0.110 | 1.0 |
| $\Delta UH_{NS}$ | 4.9 ± 0.4 | 251 ± 40 | 0.020 | 0.18 |
| $\Delta UH_{NS, 6S}$ | 8.8 ± 0.9 | 334 ± 57 | 0.026 | 0.24 |
| $\Delta UH_{NH2, 6S}$ | 2.4 ± 0.2 | 235 ± 40 | 0.010 | 0.09 |
| $\Delta U_{2S}H_{NS}$ | N.A. | N.A. | N.A. | N.A. |

*N.A., no activity was detected for $\Delta U_{2S}H_{NS}$.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled to in the art in view of the teachings set forth herein. It is, therefore, to be understood that all such variations, modifications, and changes are believed to fall within the scope of the present invention as defined by the appended claims.

We claim:

1. A method for the recombinant production of substantially pure Δ4, 5 glycuronidase, comprising:
   a) introducing into a host cell an isolated nucleic acid molecule encoding a polypeptide having Δ4, 5 glycuronidase activity, wherein the isolated nucleic acid molecule is selected from the group consisting of:
      (i) nucleic acid molecules which hybridize under stringent conditions to a nucleic acid molecule having a nucleotide sequence set forth as SEQ ID NO:2, wherein the hybridization conditions are hybridization at 65° C. in hybridization buffer comprising 3.5× (0.15M sodium chloride/0.015M sodium citrate, pH7), 0.02% Ficoll, 0.02% polyvinyl pyrrolidone, 0.02% bovine serum albumin, 25 mM $NaH_2PO_4$, pH 7, 0.5% sodium dodecylsulphate and 2 mM ethylene diamine tetra acetic acid,
      (ii) nucleic acid molecules that differ from the nucleic acid molecules of (i) in codon sequence only due to degeneracy of the genetic code, and
      (iii) full complements of (i) or (ii);
   b) expressing recombinant Δ4, 5 glycuronidase in the host cell; and
   c) isolating the recombinant Δ4, 5 glycuronidase from the host cell to produce substantially pure Δ4, 5 glycuronidase.

2. The method of claim 1, wherein the nucleic acid encodes Δ4, 5 glycuronidase comprises SEQ ID NO:2.

3. The method of claim 1, wherein the nucleic acid encodes Δ4, 5 glycuronidase comprises SEQ ID NO:4.

4. The method of claim 1, wherein the nucleic acid encodes Δ4, 5 glycuronidase having the amino acid sequences of SEQ ID NO: 1.

5. The method of claim 1, wherein the nucleic acid encodes Δ4, 5 glycuronidase having the amino acid sequences of SEQ ID NO: 3.

6. The method of claim 1, wherein the nucleic acid is operably linked to a promoter.

7. The method of claim 6, wherein an expression vector comprises the nucleic acid that is operably linked to a promoter.

8. The method of claim 7, wherein the expression vector is a prokaryotic or eukaryotic expression vector.

9. The method of claim 1, wherein the substantially pure Δ4, 5 glycuronidase is greater than about 91% free of contaminants.

10. The method of claim 1, wherein the substantially pure Δ4, 5 glycuronidase is greater than about 95% free of contaminants.

11. The method of claim 1, wherein the substantially pure Δ4, 5 glycuronidase is greater than about 99% free of contaminants.

12. The method of claim 1, wherein the recombinant Δ4, 5 glycuronidase is isolated using chromatography or electrophoresis.

13. The method of claim 1, wherein the substantially pure Δ4, 5 glycuronidase further comprises a detectable moiety, a linker molecule, a fatty acid, or a fusion protein.

14. The method of claim 1, wherein the host cell is selected from the group consisting of: yeast, fungi, insect cells, mammalian cells, *E. coli, Flavobacterium heparinum, Bacillus, Streptomyces, Pseudomonas, Salmonella, Serratia*.

15. The method of claim 7, wherein the expression vector is selected from the group consisting of: pBR322, pUC18, pUC19, ColE1, pSC101, pACYC 184, πVX, pC194, pC221, pT127, λgt10, λgt11, BPV, EBV, SV40, 2-micron circle, pMAM-neo, and pKRC.

16. The method of claim 6, wherein the promoter is selected from the group consisting of: int promoter; bla promoter; CAT promoter; bacteriophage λ ($P_L$ and $P_R$) promoter; *E. coli* promoter trp, recA, lacZ, lacI, gal; α-amylase promoter; *B. subtilis* ζ-28-specific promoter, actin promoter, collagen promoter, myosin promoter, mouse metallothionein I gene promoter; TK promoter of Herpes virus; SV40 early promoter; and yeast gal4 gene sequence promoter.

17. The method of claim 13, wherein the detectable moiety is a 6× His tag and the host cell is a bacterial cell.

18. The method of claim 17, wherein the method comprises harvesting and lysing the bacterial cell to obtain a crude lysate; fractionating and filtering the crude lysate; purifying the recombinant Δ4, 5 glycuronidase by metal chelation chromatography; and cleaving the 6× His tag with thrombin.

* * * * *

SEQUENCE LISTING

<160> NUMBER OF SEQ ID NOS: 23

<210> SEQ ID NO 1

<211> LENGTH: 382
<212> TYPE: PRT
<213> ORGANISM: Flavobacterium heparinum

<400> SEQUENCE: 1

```
Met Thr Val Thr Lys Gly Asn Gly Asp Asp Trp Leu Lys Lys Ser Thr
1               5                   10                  15

Lys Thr Ala Val Ile Gln Leu Thr Arg Ala Ala Gln Thr Tyr Thr Pro
            20                  25                  30

Gly Met Asn Pro Arg Ser Val Asn Pro Asp Gly Thr Val Arg Leu Ala
        35                  40                  45

Pro Pro Arg Asp Trp Thr Thr Gly Phe Phe Pro Gly Thr Leu Trp Tyr
    50                  55                  60

Gly Tyr Glu Leu Ser Gly Asp Lys Asn Leu Ala Ala Glu Ala Lys Arg
65                  70                  75                  80

Phe Thr Leu Ala Leu Asp Thr Ile Gln Tyr Val Lys Asp Thr His Asp
                85                  90                  95

Leu Gly Phe Met Leu Tyr Cys Ser Tyr Gly Asn Ala Tyr Arg Val Thr
            100                 105                 110

Gly Asp Lys Ile Tyr Leu Lys Pro Leu Glu Asn Gly Ala Ala Asn Leu
        115                 120                 125

Tyr Ala Arg Phe Asn Lys Lys Val Gly Ala Ile Arg Ser Trp Asp Phe
    130                 135                 140

Gly His Trp Gln Phe Pro Val Ile Ile Asp Asn Leu Met Asn Leu Glu
145                 150                 155                 160

Tyr Leu Tyr Trp Ala Gly Lys Glu Phe Asn Lys Pro Glu Trp Phe Asp
                165                 170                 175

Ala Ala Lys Thr His Ala Val Thr Thr Met Lys Asn His Phe Arg Lys
            180                 185                 190

Asp Tyr Ser Ser Tyr His Val Ile Ser Tyr Asp Thr Leu Ser Gly Lys
        195                 200                 205

Val Leu Gln Arg Glu Thr His Gln Gly Leu Thr Asn Glu Ser Ala Trp
    210                 215                 220

Ala Arg Gly Gln Ala Trp Gly Leu Tyr Gly Tyr Thr Met Ser Tyr Lys
225                 230                 235                 240

Asp Thr Lys Asp Lys Lys Phe Ile Glu His Ala Glu His Ile Ala Ala
                245                 250                 255

Phe Ile Met Asn His Pro Ala Met Pro Ala Asp Lys Ile Pro Leu Trp
            260                 265                 270

Asp Phe Asp Val His Asn Arg Asp Arg Ser Pro Arg Asp Ala Ser Ala
        275                 280                 285

Ala Ala Val Ile Ala Ser Ala Leu Leu Asp Leu Ser Thr Gln Val Lys
    290                 295                 300

Asp Gly Gln Lys Tyr Phe Lys Phe Ala Glu Asp Ile Leu Lys Thr Leu
305                 310                 315                 320

Ser Ser Asp Glu Tyr Leu Ala Lys Pro Gly Glu Asn Gln Phe Phe Ile
                325                 330                 335

Leu Lys His Ser Val Gly Ala Leu Leu Tyr Asn Ser Glu Ile Asp Thr
            340                 345                 350

Pro Leu Asn Tyr Ala Asp Tyr Tyr Leu Glu Ala Leu Lys Arg Tyr
        355                 360                 365

Ala Glu Ile Lys Lys Ile Asp Leu Lys Thr Ile Asn Gln Ser
    370                 375                 380
```

<210> SEQ ID NO 2

-continued

```
<211> LENGTH: 1149
<212> TYPE: DNA
<213> ORGANISM: Flavobacterium heparinum

<400> SEQUENCE: 2
atgacagtta cgaaaggcaa cggcgatgac tggttaaaga aatcaactaa aaccgcagta      60
atacagttaa cacgggctgc acaaacctat acaccaggca tgaacccaag gtctgtcaat     120
ccggacggga cggtaaggct ggcccctccc cgcgactgga ccacaggttt tttcccggga     180
acgttgtggt atggttatga actatcgggc gataaaaacc tggcggccga agccaaaaga     240
tttacccttg ccttagatac gatacaatat gttaaagata cgcacgacct gggctttatg     300
ttgtattgtt cttatggcaa tgcctaccgt gtaaccggag acaagattta cctgaagcca     360
ttagaaaacg gtgcggccaa tttatatgcc cgtttcaata aaaaagtagg ggccatccgc     420
tcatgggatt tcggacactg gcaatttccg gtaattatag acaacctgat gaacctggag     480
tatttatact gggcaggaaa ggaattcaat aagccagaat ggttcgatgc tgctaaaaca     540
catgcggtta cgaccatgaa aaaccatttc agaaaagatt atagttctta ccatgtgatc     600
agttacgata ccctgtctgg aaaagtactg caacgtgaaa cccatcaggg acttaccaac     660
gaatcggcct gggcacgggg gcaagcctgg ggactttacg gctataccat gagctataag     720
gatacgaaag acaaaaaatt catcgaacat gcagagcata tcgctgcttt catcatgaac     780
caccctgcaa tgccggcaga taaaattcca ctttgggact tgatgtcca caaccgcgac      840 aggtcgccaa gggatgcttc tgctgctgca gtaattgctt cagccctgct agacctgagc     900
acgcaggtaa aagatggtca gaaatatttt aaatttgccg aggatatcct gaaaacattg     960
tcatcagatg aataccctgg cgaaccccggc gagaaccagt tttttatatt gaaacatagt    1020
gtaggtgcat tgctgtacaa ttcggaaatc gatacacctt tgaattatgc cgactattac    1080
tatctggagg cttaaaaacg ctatgcagag attaaaaaaa ttgacctgaa aacaattaat    1140
cagtcttaa                                                            1149

<210> SEQ ID NO 3
<211> LENGTH: 402
<212> TYPE: PRT
<213> ORGANISM: Flavobacterium heparinum

<400> SEQUENCE: 3

Met Lys Ser Leu Leu Ser Ala Phe Val Ala Thr Ile Ala Leu Ile Gly
1               5                   10                  15

Ser Ala Asn Gly Met Thr Val Thr Lys Gly Asn Gly Asp Asp Trp Leu
            20                  25                  30

Lys Lys Ser Thr Lys Thr Ala Val Ile Gln Leu Thr Arg Ala Ala Gln
        35                  40                  45

Thr Tyr Thr Pro Gly Met Asn Pro Arg Ser Val Asn Pro Asp Gly Thr
    50                  55                  60

Val Arg Leu Ala Pro Pro Arg Asp Trp Thr Thr Gly Phe Phe Pro Gly
65                  70                  75                  80

Thr Leu Trp Tyr Gly Tyr Glu Leu Ser Gly Asp Lys Asn Leu Ala Ala
                85                  90                  95

Glu Ala Lys Arg Phe Thr Leu Ala Leu Asp Thr Ile Gln Tyr Val Lys
            100                 105                 110

Asp Thr His Asp Leu Gly Phe Met Leu Tyr Cys Ser Tyr Gly Asn Ala
        115                 120                 125

Tyr Arg Val Thr Gly Asp Lys Ile Tyr Leu Lys Pro Leu Glu Asn Gly
    130                 135                 140
```

Ala Ala Asn Leu Tyr Ala Arg Phe Asn Lys Lys Val Gly Ile Arg
145                 150                 155                 160

Ser Trp Asp Phe Gly His Trp Gln Phe Pro Val Ile Asp Asn Leu
            165                 170                 175

Met Asn Leu Glu Tyr Leu Tyr Trp Ala Gly Lys Glu Phe Asn Lys Pro
        180                 185                 190

Glu Trp Phe Asp Ala Ala Lys Thr His Ala Val Thr Thr Met Lys Asn
            195                 200                 205

His Phe Arg Lys Asp Tyr Ser Ser Tyr His Val Ile Ser Tyr Asp Thr
    210                 215                 220

Leu Ser Gly Lys Val Leu Gln Arg Glu Thr His Gln Gly Leu Thr Asn
225                 230                 235                 240

Glu Ser Ala Trp Ala Arg Gly Gln Ala Trp Gly Leu Tyr Gly Tyr Thr
                245                 250                 255

Met Ser Tyr Lys Asp Thr Lys Asp Lys Lys Phe Ile Glu His Ala Glu
            260                 265                 270

His Ile Ala Ala Phe Ile Met Asn His Pro Ala Met Pro Ala Asp Lys
    275                 280                 285

Ile Pro Leu Trp Asp Phe Asp Val His Asn Arg Asp Arg Ser Pro Arg
290                 295                 300

Asp Ala Ser Ala Ala Ala Val Ile Ala Ser Ala Leu Leu Asp Leu Ser
305                 310                 315                 320

Thr Gln Val Lys Asp Gly Gln Lys Tyr Phe Lys Phe Ala Glu Asp Ile
                325                 330                 335

Leu Lys Thr Leu Ser Ser Asp Glu Tyr Leu Ala Lys Pro Gly Glu Asn
            340                 345                 350

Gln Phe Phe Ile Leu Lys His Ser Val Gly Ala Leu Leu Tyr Asn Ser
    355                 360                 365

Glu Ile Asp Thr Pro Leu Asn Tyr Ala Asp Tyr Tyr Leu Glu Ala
370                 375                 380

Leu Lys Arg Tyr Ala Glu Ile Lys Lys Ile Asp Leu Lys Thr Ile Asn
385                 390                 395                 400

Gln Ser

<210> SEQ ID NO 4
<211> LENGTH: 1209
<212> TYPE: DNA
<213> ORGANISM: Flavobacterium heparinum

<400> SEQUENCE: 4
atgaaatcac tactcagtgc gtttgttgcg actattgcat taataggatc tgcaaacggg      60
atgacagtta cgaaaggcaa cggcgatgac tggttaaaga aatcaactaa aaccgcagta     120
atacagttaa cacgggctgc acaaacctat acaccaggca tgaacccaag gtctgtcaat     180
ccggacggga cggtaaggct ggccccctcc cgcgactgga ccacaggttt tttcccggga     240
acgttgtggt atggttatga actatcgggc gataaaaacc tggcggccga agccaaaaga     300
tttacccttg ccttagatac gatacaatat gttaaagata cgcacgacct gggctttatg     360
ttgtattgtt cttatggcaa tgcctaccgt gtaaccggag acaagattta cctgaagcca     420
ttagaaaacg gtgcggccaa tttatatgcc cgtttcaata aaaaagtagg ggccatccgc     480
tcatgggatt tcggacactg gcaatttccg gtaattatag acaacctgat gaacctggag     540
tatttatact gggcaggaaa ggaattcaat aagccagaat ggttcgatgc tgctaaaaca     600
catgcggtta cgaccatgaa aaaccatttc agaaaagatt atagttctta ccatgtgatc     660

-continued

```
agttacgata ccctgtctgg aaaagtactg caacgtgaaa cccatcaggg acttaccaac    720
gaatcggcct gggcacgggg gcaagcctgg ggactttacg gctataccat gagctataag    780
gatacgaaag acaaaaaatt catcgaacat gcagagcata tcgctgcttt catcatgaac    840
caccctgcaa tgccggcaga taaaattcca ctttgggact tgatgtccaa caaccgcgac    900
aggtcgccaa gggatgcttc tgctgctgca gtaattgctt cagccctgct agacctgagc    960
acgcaggtaa aagatggtca gaaatatttt aaatttgccg aggatatcct gaaaacattg   1020
tcatcagatg aataccctgg cgaaacccgg cgagaaccagt tttttatatt gaaacatagt  1080
gtaggtgcat tgctgtacaa ttcggaaatc gatacacctt tgaattatgc cgactattac   1140
tatctggagg ctttaaaacg ctatgcagag attaaaaaaa ttgacctgaa aacaattaat   1200
cagtcttaa                                                           1209
```

<210> SEQ ID NO 5
<211> LENGTH: 27
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: (6)..(6)
<223> OTHER INFORMATION: n = a, g, c or t/u
<220> FEATURE:
<221> NAME/KEY: misc_feature
<222> LOCATION: (15)..(15)
<223> OTHER INFORMATION: n = a, g, c or t/u
<220> FEATURE:
<221> NAME/KEY: misc_feature
<222> LOCATION: (18)..(18)
<223> OTHER INFORMATION: n = a, g, c or t/u
<220> FEATURE:
<221> NAME/KEY: misc_feature
<222> LOCATION: (21)..(21)
<223> OTHER INFORMATION: n = a, g, c or t/u

<400> SEQUENCE: 5
garacncayc arggnytnac naaygar                                         27

<210> SEQ ID NO 6
<211> LENGTH: 27
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: (7)..(7)
<223> OTHER INFORMATION: n = a, g, c or t/u
<220> FEATURE:
<221> NAME/KEY: misc_feature
<222> LOCATION: (10)..(10)
<223> OTHER INFORMATION: n = a, g, c or t/u
<220> FEATURE:
<221> NAME/KEY: misc_feature
<222> LOCATION: (13)..(13)
<223> OTHER INFORMATION: n = a, g, c or t/u
<220> FEATURE:
<221> NAME/KEY: misc_feature
<222> LOCATION: (22)..(22)
<223> OTHER INFORMATION: n = a, g, c or t/u

<400> SEQUENCE: 6
ytcrttngtn arnccytgrt gngtytc                                         27

<210> SEQ ID NO 7
<211> LENGTH: 21

```
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: (9)..(9)
<223> OTHER INFORMATION: n = a, g, c or t/u

<400> SEQUENCE: 7
aaytaygcng aytaytayta y                                         21

<210> SEQ ID NO 8
<211> LENGTH: 21
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: (13)..(13)
<223> OTHER INFORMATION: n = a, g, c or t/u

<400> SEQUENCE: 8
rtartartar tcngcrtart t                                         21

<210> SEQ ID NO 9
<211> LENGTH: 24
<212> TYPE: DNA
<213> ORGANISM: Artificial Sequence
<220> FEATURE:
<223> OTHER INFORMATION: Degenerate Primer
<220> FEATURE:
<221> NAME/KEY: misc_feature
<222> LOCATION: (6)..(6)
<223> OTHER INFORMATION: n = a, g, c or t/u
<220> FEATURE:
<221> NAME/KEY: misc_feature
<222> LOCATION: (12)..(12)
<223> OTHER INFORMATION: n = a, g, c or t/u
<220> FEATURE:
<221> NAME/KEY: misc_feature
<222> LOCATION: (15)..(15)
<223> OTHER INFORMATION: n = a, g, c or t/u
<220> FEATURE:
<221> NAME/KEY: misc_feature
<222> LOCATION: (18)..(18)
<223> OTHER INFORMATION: n = a, g, c or t/u

<400> SEQUENCE: 9
caracntaya cnccnggnat gaay                                      24

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ttcatggtcg taaccgcatg                                           20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11 tataccaccag gcatgaaccc                                          20
```

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cccagtataa atactccagg t                                              21

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
tgttctagac atatgaaatc actactcagt gc                                  32

<210> SEQ ID NO 14
<211> LENGTH: 32
<212> TYPE: DNA
<213> ORGANISM: Artificial Sequence
<220> FEATURE:
<223> OTHER INFORMATION: Primer

<400> SEQUENCE: 14
gtctcgagga tccttaagac tgattaattg tt                                  32

<210> SEQ ID NO 15
<211> LENGTH: 32
<212> TYPE: DNA
<213> ORGANISM: Artificial Sequence
<220> FEATURE:
<223> OTHER INFORMATION: Primer

<400> SEQUENCE: 15
tgttctagac atatgacagt tacgaaaggc aa                                  32

<210> SEQ ID NO 16
<211> LENGTH: 17
<212> TYPE: PRT
<213> ORGANISM: Artificial Sequence
<220> FEATURE:
<223> OTHER INFORMATION: Cleaved N-terminal 6X His Tagged Peptide

<400> SEQUENCE: 16

Met Gly Ser Ser His His His His His His Ser Ser Gly Leu Val Pro
1               5                   10                  15

Arg

<210> SEQ ID NO 17
<211> LENGTH: 12
<212> TYPE: PRT
<213> ORGANISM: Artificial Sequence
<220> FEATURE:
<223> OTHER INFORMATION: Motif Sequence
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(6)
<223> OTHER INFORMATION: Xaa = any amino acid
<220> FEATURE:

```
<221> NAME/KEY: MISC_FEATURE
<222> LOCATION: (8)..(11)
<223> OTHER INFORMATION: Xaa = any amino acid

<400> SEQUENCE: 17

Ala Xaa Xaa Ala Xaa Xaa Ala Xaa Xaa Xaa Xaa Ala
1               5                   10

<210> SEQ ID NO 18
<211> LENGTH: 12
<212> TYPE: PRT
<213> ORGANISM: Flavobacterium heparinum

<400> SEQUENCE: 18

Glu Phe Asn Lys Pro Glu Trp Phe Asp Ala Ala Lys
1               5                   10

<210> SEQ ID NO 19
<211> LENGTH: 10
<212> TYPE: PRT
<213> ORGANISM: Flavobacterium heparinum

<400> SEQUENCE: 19

Pro Gly Glu Asn Gln Phe Phe Ile Leu Lys
1               5                   10

<210> SEQ ID NO 20
<211> LENGTH: 12
<212> TYPE: PRT
<213> ORGANISM: Flavobacterium heparinum

<400> SEQUENCE: 20

Phe Thr Leu Ala Leu Asp Thr Ile Gln Tyr Val Lys
1               5                   10

<210> SEQ ID NO 21
<211> LENGTH: 32
<212> TYPE: PRT
<213> ORGANISM: Flavobacterium heparinum

<400> SEQUENCE: 21

Val Leu Gln Arg Glu Thr His Gln Gly Leu Thr Asn Glu Ser Ala Trp
1               5                   10                  15

Ala Arg Gly Gln Ala Trp Gly Leu Tyr Gly Tyr Thr Met Ser Tyr Lys
            20                  25                  30

<210> SEQ ID NO 22
<211> LENGTH: 28
<212> TYPE: PRT
<213> ORGANISM: Flavobacterium heparinum

<400> SEQUENCE: 22

His Ser Val Gly Ala Leu Leu Tyr Asn Ser Glu Ile Asp Thr Pro Leu
1               5                   10                  15

Asn Tyr Ala Asp Tyr Tyr Tyr Leu Glu Ala Leu Lys
            20                  25

<210> SEQ ID NO 23
<211> LENGTH: 34
<212> TYPE: PRT
<213> ORGANISM: Flavobacterium heparinum

<400> SEQUENCE: 23

Thr Ala Val Ile Gln Leu Thr Arg Ala Ala Gln Thr Tyr Thr Pro Gly
1               5                   10                  15
```

-continued

```
Met Asn Pro Arg Ser Val Asn Pro Asp Gly Thr Val Arg Leu Ala Pro
             20                  25                  30
Pro Arg
```